United States Patent
Deming et al.

(10) Patent No.: US 12,090,206 B2
(45) Date of Patent: Sep. 17, 2024

(54) COMPOSITIONS COMPRISING TRI- AND PENTA-BLOCK SYNTHETIC COPOLYPEPTIDE HYDROGELS

(71) Applicant: The Regents of the University of California, Oakland, CA (US)

(72) Inventors: Timothy J. Deming, Los Angeles, CA (US); Yintao Sun, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 518 days.

(21) Appl. No.: 17/238,632

(22) Filed: Apr. 23, 2021

(65) Prior Publication Data

US 2021/0330795 A1    Oct. 28, 2021

Related U.S. Application Data

(60) Provisional application No. 63/014,446, filed on Apr. 23, 2020.

(51) Int. Cl.
| | | |
|---|---|---|
| A61K 47/34 | (2017.01) | |
| C07K 14/00 | (2006.01) | |
| C08G 69/10 | (2006.01) | |
| C08L 77/04 | (2006.01) | |

(52) U.S. Cl.
CPC .............. *A61K 47/34* (2013.01); *C07K 14/00* (2013.01); *C08G 69/10* (2013.01); *C08L 77/04* (2013.01)

(58) Field of Classification Search
CPC .......... A61K 47/34; C07K 14/00; C08L 77/04
See application file for complete search history.

(56) References Cited

U.S. PATENT DOCUMENTS

| | | | |
|---|---|---|---|
| 4,554,101 A | 11/1985 | Hopp | |
| 5,670,483 A | 9/1997 | Zhang et al. | |
| 5,856,308 A | 1/1999 | St. Pierre et al. | |
| 6,361,768 B1 | 3/2002 | Galleguillos et al. | |
| 6,686,446 B2 | 2/2004 | Deming et al. | |
| 7,279,458 B2 | 10/2007 | Fatheree et al. | |
| 7,846,445 B2 | 12/2010 | Schellenberger et al. | |
| 8,691,204 B2 | 4/2014 | Deming et al. | |
| 9,017,730 B2 | 4/2015 | Bevilacqua et al. | |
| 10,448,634 B2 | 10/2019 | Bevilacqua et al. | |
| 2002/0032309 A1 | 3/2002 | Deming et al. | |
| 2003/0147958 A1 | 8/2003 | Ahn et al. | |
| 2003/0176335 A1 | 9/2003 | Zhang et al. | |
| 2005/0031522 A1 | 2/2005 | Delaney et al. | |
| 2005/0042753 A1 | 2/2005 | Yang et al. | |
| 2005/0079159 A1 | 4/2005 | Shastri et al. | |
| 2006/0240092 A1 | 10/2006 | Breitenkamp et al. | |
| 2007/0099840 A1 | 5/2007 | Ulijn et al. | |
| 2007/0157967 A1 | 7/2007 | Mershin et al. | |
| 2007/0190110 A1 | 8/2007 | Pameijer et al. | |
| 2008/0003288 A1 | 1/2008 | Bromberg et al. | |
| 2008/0125581 A1 | 5/2008 | Deming et al. | |
| 2008/0166388 A1 | 7/2008 | Palecek et al. | |
| 2008/0176807 A1 | 7/2008 | DeGrado et al. | |
| 2008/0243049 A1 | 10/2008 | Hardy | |
| 2009/0028832 A1 | 1/2009 | Chung et al. | |
| 2009/0105341 A1 | 4/2009 | Stanton | |
| 2009/0175785 A1 | 7/2009 | Gazit et al. | |
| 2009/0208548 A1 | 8/2009 | Mason et al. | |
| 2010/0003336 A1 | 1/2010 | Deming et al. | |
| 2010/0222407 A1 | 9/2010 | Segura et al. | |
| 2012/0093722 A1 | 4/2012 | Deming et al. | |
| 2012/0178676 A1 | 7/2012 | Barrack et al. | |
| 2013/0202711 A1 | 8/2013 | Kataoka et al. | |
| 2014/0286865 A1 | 9/2014 | Deming et al. | |
| 2015/0258219 A1 | 9/2015 | Kataoka et al. | |
| 2016/0002405 A1 | 1/2016 | Deming et al. | |
| 2020/0246503 A1 | 8/2020 | Deming et al. | |
| 2021/0330795 A1 | 10/2021 | Deming et al. | |
| 2022/0177704 A1 | 6/2022 | Deming et al. | |

FOREIGN PATENT DOCUMENTS

| | | |
|---|---|---|
| WO | WO-01/94379 A2 | 12/2001 |
| WO | WO-2006/113667 A1 | 10/2006 |
| WO | WO-2008/070571 A2 | 6/2008 |
| WO | WO-2009/025802 A1 | 2/2009 |
| WO | WO-2010/096572 A2 | 8/2010 |
| WO | WO-2012/027411 A2 | 3/2012 |
| WO | WO-2014/134203 A1 | 9/2014 |
| WO | WO-2019/067676 A1 | 4/2019 |
| WO | WO-2020/198644 A1 | 10/2020 |

OTHER PUBLICATIONS

Captain et al., "Methionine sulfoxide and phosphonate containing double hydrophilic block copolypeptides and their mineralization of calcium carbonate," Journal of Polymer Science Part A: Polymer Chemistry, 54(23): 3707-3712 (2016).

Extended European Search Report for EP Application No. 18861462.2 dated Aug. 23, 2021.

Xu et al., "Thermosensitive Polypeptide Hydrogels as a platform for ROS-triggered cargo release with innate cytoprotective ability under oxidative stress," Advanced Healthcare Materials, 5(1): 1979-1990 (2016).

Cui et al., "High performance and reversible ionic polypeptide hydrogel based on charge-driven assembly for biomedical applications," Acta Biomaterialia, 11: 183-190 (2015).

Harada et al., "Formation of Polyion Complex Micelles in an Aqueous Milieu from a Pair of Oppositely-Charged Block Copolymers with Poly(ethylene glycol) Segments," Macromolecules, 28: 5294-5299 (1995).

(Continued)

*Primary Examiner* — Gyan Chandra

(74) *Attorney, Agent, or Firm* — Foley Hoag LLP; David P. Halstead; Alexander J. Chatterley

(57) ABSTRACT

Disclosed herein are mixtures of triblock or pentablock copolypeptide hydrogels (DCH). These hydrogels possess improved mechanical properties, such as elasticity, that are synergistically increased over the individual component DCHs, to greater than would be expected for a linear combination of the components. Also disclosed herein are methods of making and using the triblock and pentablock copolypeptide hydrogels.

22 Claims, 5 Drawing Sheets

(56) References Cited

OTHER PUBLICATIONS

Insua et al., "Polyion complex (PIC) particles: Preparation and biomedical applications," European Polymer Journal, 81: 198-215 (2016).
Kishimura., "Development of polyion complex vesicles (PICsomes) from block copolymers for biomedical applications," Polymer Journal, 45: 892-897 (2013).
Livingstone et al., "Protein sequence alignments," CABIOS, 9(6): 745-756 (1993).
Srivastava et al., "Gel phase formation in dilute triblock copolyelectrolyte complexes," Nature Communications, 8(14131): 9 pages (2017).
Strohl., "Fusion Proteins for Half-Life Extension of Biologics as a Strategy to Make Biobetters," BioDrugs, 29: 215-239 (2015).
Taylor., "The Properties of Amino Acids in Sequences," Biological Technique Series, Genetic Database: 81-103 (1997).
Wagner et al., "New Naturally Occurring Amino Acids," Angew. Chem. Int. Ed. Engl., 22: 816-828 (1983).
Arunan et al., "Definition of the hydrogen bond (IUPAC Recommendations 2011)," Pure Appl. Chem., 83(8): 1637-1641 (Jul. 2011).
Captain et al., "Methionine sulfoxide and phosphonate containing double hydrophilic block copolypeptides and their mineralization of calcium carbonate," Journal of Polymer Science Part A: Polymer Chemistry, 54(23): 3707-3712 (Sep. 7, 2016).
Chassenieux et al., "Recent trends in pH/thermo-responsive self-assembling hydrogels: from polyions to peptide-based polymeric gelators," Soft Matter, 12(5):1344-1359 (Jan. 5, 2016).
Xu et al., "Thermosensitive Polypeptide Hydrogels as a platform for ROS-triggered cargo release with innate cytoprotective ability under oxidative stress," Advanced Healthcare Materials, 5(1): 1979-1990 (Jun. 10, 2016).
Yinato Sun., "Study of Polyion Complex Structure Formation from Mixing Oppositely-Charged Block Copolypeptides," Dissertation for Degree of Docket of Philosophy in Bioengineering, University of California Los Angeles: 132 pages (Apr. 19, 2019).
AU 2011 293468 Examination Report dated Dec. 10, 2013.
Bani-Jaber et al., "Efficacy of the antimicrobial peptide nisin in emulsifying oil in water," J Food Sci, 65(3):502-6 (2000).
Bellomo et al., "Stimuli-responsive polypeptide vesicles by conformation-specific assembly," Nat Mater 3:244-248 (2004).
Bermudez et al., "Molecular weight dependence of polymersome membrane structure, elasticity, and stability," Macromol, 35:8203-8 (2002).
Boateng et al., "Wound Healing Dressings and Drug Delivery Systems: A Review," J Pharm Sci, 97(8):2892-2923 (2008).
Boyce et al., "Guideline for hand hygiene in health-care settings," Morbidity and Mortality Weekly Report, 51(RR-16):1-54 (2002).
Brogden et al., "Antimicrobial peptides: Pore formers or metabolic inhibitors in bacteria?" Nat Rev Microbiol, 3(3):238-50 (2005).
Brooks et al., "Tat peptide-mediated cellular delivery: back to basics," Adv Drug Deliv Rev, 57:559-77 (2005).
CA 2,809,093 Examination Report dated Mar. 31, 2014.
Calnan et al., "Arginine-mediated RNA recognition: the arginine fork," Science, 252:1167-71 (1991).
Carlsen et al., "Self-assembly of polypeptide-based block copolymer amphiphiles," Current Opinion in Colloid & Interface Science, 14(5):329-339 (2009).
Chassenieux et al., "Recent trends in pH/thermo-responsive self-assembling hydrogels: from polyions to peptide-based polymeric gelators," Soft Matter, 12(5):1344-1359 (2016).
CN 201180051224 Examination Report datd May 8, 2014.
Deming et al., "Methodologies for preparation of synthetic block copolypeptides: Materials with future promise in drug delivery," Adv Drug Deliver Rev, 54:1145-55 (2002).
Deming et al., "Polypeptide and polypeptide hybrid copolymer synthesis via NCA polymerization," ChemInform, 38(5):1-18 (2007).
Deming et al., "Synthetic polypeptides for biomedical applications," Prog Polym Sci, 32:858-75 (2007).
Deming, "Cobalt and iron initiators for the controlled polymerization of alpha-amino acid-N-carboxyhanhydrides," Macromol, 32:4500-2 (1999).
Deming, "Facile synthesis of block copolypeptides of defined architecture," Nature, 390:386-9 (1997).
Discher et al., "A. Polymer vesicles," Science, 297:967-73 (2002).
Discher et al., "Polymer vesicles in various media," Curr Opin Coll Interface Sci, 5:125-45 (2000).
Dondoni et al., "The emergence of thiol-ene coupling as a click process for materials and bioorganic chemistry," Angew Chem Int Ed Engl., 47(47):8995-7 (2008).
Eberlein et al., "Clinical use of polihexanide on acute and chronic wounds for antisepsis and docontamination," Skin Pharmacol Physiol, 23(Suppl.):45-51 (2010).
Epand et al., "Dual mechanism of bacterial lethality for a cationic sequence-random copolymer that mimics host-defense antimicrobial peptides," J Mol Biol, 379(1):38-50 (2008).
Extended European Search Report dated Nov. 9, 2012 in European Application No. 10744302.0.
Futaki, "Membrane-permeable arginine-rich peptides and the translocation mechanisms," Adv Drug Deliv Rev, 57:547-58 (2005).
Gabriel et al., "Infectious Disease: Connecting innate immunity to biocidal polymers," Mater Sci Eng R Rep, 57(1-6):28-64 (2007).
Gilbert et al., "Cationic antiseptics: Diversity of action under a common epithet," J Applied Microbiol, 99(4):703-15 (2005).
Ginsburg et al., "Action of polylysine on the fibrinolytic reaction," Bulletin of the Research Council of Israel, 4:51-6 (1954).
Goodson et al., "Characterization of novel antimicrobial peptoids," Antimicrob Agents Chemother, 43(6):1429-34 (1999).
Hancock et al., "Cationic peptides: A new source of antibiotics," Trends Biotechnol, 16(2):82-8 (1998).
Hanson et al., "Nanoscale double emulsions stabilized by single-component block copolypeptides," Nature, 455:85-9 (2008).
Higgins et al., "Resistance to antibiotics and biocides among non-fermenting gram-negative bacteria," Clin Microbiol Infections, 7:308-15 (2001).
Ho et al., "Improving emulsifying activity of [var epsilon]-polylysine by conjugation with dextran through the Maillard reaction," Food Chem, 68(4):449-55 (2000).
Holowka et al., "Charged polypeptide vesicles with controllable diameter," J Am Chem Soc, 127(35):12423-8 (2005).
Hou et al., "The repair of brain lesion by implamantation of hyaluronic acid hydrogels modified with laminin," J Neurosci Meth, 148(1):60-70 (2005).
Ilker et al., "Tuning the hemolytic and antibacterial activities of amphiphilic polynorbornene derivatives," J Am Chem Soc, 126(48):15870-5 (2004).
Indian Office Action dated Feb. 22, 2013 issued in Application No. 1231/mumnp/2009.
International Search Report and a Written Opinion of the International Searching Authority issued in Application No. PCT/US2010/24603, dated Sep. 28, 2010.
International Search Report and Written Opinion for International Application No. PCT/US2018/053050 dated Jan. 21, 2019.
International Search Report and Written Opinion for International Application No. PCT/US2020/025377 dated Jul. 16, 2020.
International Search Report and Written Opinion issued by the International Searching Authority in corresponding International Application No. PCT/US2011/048869, dated Mar. 28, 2012.
International Search Report issued in PCT Application No. PCT/US2011/048869 dated Sep. 28, 2012.
Japanese Office Action dated Nov. 27, 2012, issued in Japanese Patent Application No. 2009-539522.
Jenkins et al., "Interactions of polylysine with platelets," Blood, 37(4):395-412 (1971).
JP 2013-526108 Examination Report dated Jun. 10, 2014.
Kar et al., "Synthesis and characterization of poly-L-lysine-grafted silica nanoparticles synthesized via NCA polymerization and click chemistry," Langmuir, 26(8):5772-81 (2010).
Kim et al., "Pharmacodynamics of insulin in polyethylene glycol-coated liposomes," Int J Pharm, 180:75-81 (1999).
Kuroda et al., "The role of hydrophobicity in the antimicrobial and hemolytic activities of polymethacrylate derivatives," Chem, 15(5):1123-33 (2009).

(56) References Cited

OTHER PUBLICATIONS

Lam et al., "D-amino acids govern stationary phase cell wall remodeling in bacteria," Science, 325(5947):1552-5 (2009).
Landman et al., "Polymyxins revisited," Clin Microbiol Rev, 21(3):449-65 (2008).
Lin et al., "Chondroitinase ABC has a long-lasting effect on chondroitin sulphate glycosaminoglycan content in the injured rat brain," J Neurochem, 104(2):400-8 (2008).
Lio et al., "Topical antibacterial agents," Infect Dis Clin N Am, 23(4):945-63 (2009).
Liu et al., "De novo design, synthesis, and characterization of antimicrobial beta-peptides," J Am Chem Soc, 123(31):7553-9 (2001).
Liu et al., "Nontoxic membrane-active antimicrobial arylamide oligomers," Angew Chem Int Ed Engl, 43(9):1158-62 (2004).
Mackman et al., "Role of the Extrinsic Pathway of Blood Coagulation in Hemostasis and Thrombosis," Arterisocler Thromb Vasc Biol, 27: 1687-1693 (2007).
Mitchell et al., "Polyarginine enters cells more efficiently than other polycationic homopolymers," J Peptide Res, 56:318-25 (2000).
Mosmann, "Rapid colorimetric assay for cellular growth and survival: Application to proliferation and cytotoxicity assays," J Immunol Meth, 65:55-63 (1983).
Murriel et al., "Influence of protein transduction on intracellular delivery of macromolecules," Expert Opin Drug Deliv, 3(6):739-46 (2006).
Nowak et al., "Rapidly recovering hydrogels scaffolds from self-assembling diblock copolypeptide amphiphiles," Nature, 417(6887):424-8 (2002).
Oie et al., "Microbial contamination of antiseptics and disinfectants," Am J Infect Control, 24(5):389-95 (1996).
Pakstis et al., "Effect of chemistry and morphology on the biofunctionality of self-assembling diblock copolypeptide hydrogels," Biomacromol, 5:312-8 (2004).
Pandey et al., "Glycopolypeptide-Grafted Bioactive Polyionic Complex Vesicles (PICsomes) and Their Specific Polyvalent Interactions," ACS Omega, 1(4):600-612 (2016).
Picout et al., "Rheology of biopolymer solutions and gels," The Scientific World Journal, 3:105-21 (2003).
Porter et al., "Mimicry of host-defense peptides by unnatural oligomers: Antimicrobial beta-peptides," J Am Chem Soc, 124(25):7324-30 (2002).
Proctor, "Blood substitutes and experimental models of trauma," J Trauma, 54:S106 (2003).
Rabinovici et al., "Liposome-encapsulated hemoglobin: an oxygen-carrying fluid," Circulatory Shock, 32:1 (1990).
Riess, "Oxygen carriers ("blood substitutes")—raison d'etre, chemistry, and some physiology," Chem Rev 101(9):2797-920 (2001).
Rodriguez et al., "Enzyme-triggered cargo release from methionine sulfoxide containing copolypeptide vesicles," Biomacromolecules, 14(10):3610-3614 (2013).
Rothbard et al., "Adaptive translocation: The role of hydrogen bonding and membrane potential in the uptake of guanidinium-rich transporters into cells," Adv Drug Deliv Rev, 57:495-504 (2005).
Rothbard et al., "Conjugation of arginine oligomers to cyclosporin A facilitates topical delivery and inhibition of inflammation," Nat Med, 6:1253-7 (2000).
Rothbard et al., "Role of membrane potential hydrogen bonding in the mechanism of translocation of guanidinium-rich peptides into cells," J Am Chem Soc, 126:9506-7 (2004).
Sakai et al., "Anion-mediated transfer of polyarginine across liquid and bilayer membranes," J Am Chem Soc, 125:14348-56 (2003).
Salick et al., "Inherent antibacterial activity of a peptide-based beta-hairpin hydrogel," J Am Chem Soc, 129(47): 14793-9 (2007).
Sela et al., "Biological properties of poly amino acids," Adv Protein Chem, 14:391-478 (1959).
SG 201310360-2 Examination Report dated Jun. 24, 2014.
Song et al., "Sustained local delivery of bioactive nerve growth factor in the central nervous system via tunable diblock copolypeptide hydrogel depots," Biomater, 33:9105-16 (2012).
Stickler et al., "Antiseptic and antibiotic resistance in gram-negative bacteria causing urinary tract infection," J Clin Pathol, 33(3):288-96 (1980).
Sun et al., "Conformation-Directed Formation of Self-Healing Diblock Copolypeptide Hydrogels via Polyion Complexation," Journal of the American Chemical Society, 139(42):15114-15121 (2017).
Supplementary European Search Report dated Nov. 9, 2012.
Tew et al., "Antimicrobial activity of an abiotic host defense peptide mimic," Biochim Biophys Acta, 1758(9):1387-92 (2006).
Tian et al., "Hyaluronic acid-poly-D-lysine-based three-dimensional hydrogel for traumatic brain injury," Tissue Eng, 11(3-4):513-25 (2005).
Tian et al., "Polypeptide based vesicles: formation, properties and application for drug delivery," Journal of Materials Chemistry, 22(34):17404-17414 (2012).
Tjong et al., "Prediction of Protein Solubility from Calculation of Transfer Free Energy," Biophys J, 95(6): 2601-2609 (2008).
Torchilin et al., "TAT peptide on the surface of liposomes affords their efficient intracellular delivery even at low temperature and in the presence of metabolic inhibitors," Proc Natl Acad Sci USA, 98:9786-91 (2001).
Tseng et al., "Translocation of liposomes into cancer cells by cell-penetrating peptides Peenetratin and Tat: A kinetic and efficacy study," Mol Pharmacol, 62:864-72 (2002).
Wadia et al., "Transducible TAT-HA fusogenic peptide enhances escape of TAT-fusion proteins after lipid raft macropinocytosis," Nat Med, 10:310-5 (2004).
Wadia et al., "Transmembrane delivery of protein and peptide drugs by TAT-mediated transduction in the treatment of cancer," Adv Drug Deliv Rev, 57:579-596 (2005).
Wang et al., "Antimicrobial and hemolytic activities of copolymers with cationic and hydrophobic groups: A comparison of block and random copolymers," Macromol Biosci, 11(11):1499-504 (2011).
Wyrsta et al., "A parallel synthetic approach for the analysis of membrane interactive copolypeptides," J Am Chem Soc, 123(51):12919-20 (2001).
Wyrsta et al., "Synthesis and Studies of Polypeptide Materials: Self-assembled Block Copolypepetide Amphiphiles, DNA-condensing Block Copolypeptides and Membrane-interactive Random Copolypeptides," University of California, Santa Barbara, p. 125 (2002).
Xu et al., "Amphiphilic poly (amino acid) based micelles applied to drug delivery: The in vitro and in vivo challenges and the corresponding potential strategies," Journal of Controlled Release, 199:84-97 (2014).
Yang et al., "Biocompatibility of amphiphilic diblock copolypeptide hydrogels in the central nervous system," Biomaterials, 30(15):2881-98 (2009).
Yeaman et al., "Mechanisms of antimicrobial peptide action and resistance," Pharmacol Rev, 55(1):27-55 (2003).
Zaiou et al., "Multifunctional antimicrobial peptides: Therapeutic targets in several human diseases," J Mol Med (Berl), 85(4):317-29 (2007).
Zasloff et al., "Antimicrobial peptides of multicellular organisms," Nature, 415(6870):389-95 (2002).
Zhang et al., "Design and synthesis of nonionic copolypeptide hydrogels with reversible thermoresponsive and tunable physical properties," Biomacromol, 16:1331-40 (2015).
Zhang et al., "Supramolecular hydrogels assembled from nonionic poly (ethylene glycol)-b-polypeptide diblocks containing oegylated poly-L-glutamate," Polym Chem, 5:3346-51 [e-pub] (2014).
Zhang et al., "Thermoresponsive copolypeptide hydrogel vehicles for central nervous system cell delivery," ACS Biomater Sci Eng, 1:705-17 (2015).
Zhang et al., "Tunable diblock copolypeptide hydrogel depots for local delivery of hydrophobic molecules in healthy and injured central nervous system," Biomater, 35:1989-2000 (2014).
Zhou et al., "High potency and broad-spectrum antimicrobial peptides synthesized via ring-opening polymerization of alpha-aminoacid-N-carboxyanhydrides," Biomacromolecules, 11(1):60-7 (2010).
Deming., "Synthesis of Side-Chain Modified Polypeptides" Chemical Reviews, 116:786-808 (2016).

(56) References Cited

OTHER PUBLICATIONS

Krogstad et al., "Effects of Polymer and Salt Concentration on the Structure and Properties of Triblock Copolymer Coacervate Hydrogels" Macromolecules, 26: 1512-1518 (2013).

Papadakis et al., "Responsive Hydrogels from Associative Block Copolymers: Physical Gelling through Polyion Complexation" Gels, vol. 3 (2017).

Pitha et al., "Poly-L-methionine Sulfoxide: A Biologically Inert Analogue of Dimethyl Sulfoxide with Solubilizing Potency" Journal of Pharmaceutical Sciences, vol. 72, No. 6 (1983).

Schellenberger et al., "A recombinant polypeptide extends the in vivo half-life of peptides and proteins in a tunable manner" Nature Biotechnology, 27(12): 1186-1190 (2009).

Extended European Search Report for EP Application No. 20779898.4 dated Jul. 17, 2023.

Jenkins et al., "Glossary of Basic Terms in Polymer Science (IUPAC Recommendations 1996)", Pure and Applied Chemistry 68.12: 2287-2311 (1996).

Diblocks (DB)

$(M^OA)_{100}E_{30} + (M^OA)_{100}K_{30}$

Triblocks (TB)

$(M^OA)_{50}E_{30}(M^OA)_{50} + (M^OA)_{50}K_{30}(M^OA)_{50}$

Pentablocks (PB)

$(M^OA)_{50}E_{30}(M^OA)_{100}E_{30}(M^OA)_{50}$
+
$(M^OA)_{50}K_{30}(M^OA)_{100}K_{30}(M^OA)_{50}$

COMPOSITIONS COMPRISING TRI- AND PENTA-BLOCK SYNTHETIC COPOLYPEPTIDE HYDROGELS

RELATED APPLICATIONS

This application claims the benefit of U.S. Provisional Patent Application No. 63/014,446, filed on Apr. 23, 2020, the contents of which are hereby incorporated by reference in their entirety.

BACKGROUND

Polyion complex (PIC) assembly of dual hydrophilic block copolymers containing non-ionic and oppositely charged ionic segments has been developed as a facile method to prepare a diverse array of micelles, vesicles, and hydrogels in aqueous media. Due to the high water solubility of precursors, PIC formation allows the preparation of supramolecular assemblies at high concentrations via simple mixing, and does not require the use of either heating or cosolvents. These assemblies are experiencing extensive development in applications, including as carriers for therapeutic molecules and as scaffolds for cell culture and tissue repair. Therefore, there remains a need for PIC systems with improved mechanical properties, stability in media, and ability to encapsulate and release any type of molecule or cell.

SUMMARY OF THE INVENTION

In one aspect, the present disclosure provides a composition comprising a first copolypeptide comprising Substructure I, and a second copolypeptide comprising Substructure II, and water, wherein Substructure I is depicted as follows:

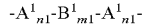   Substructure I;

Substructure II is depicted as follows:

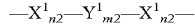   Substructure II;

each instance of $A^1$ is an amino acid residue independently selected from a non-ionic, hydrophilic amino acid, sarcosine, glycine, and alanine;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1 and n2 is independently about 25 to about 600;
m1 and m2 are independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked. In another aspect, the present disclosure provides composition comprising a first copolypeptide comprising Substructure III, and a second copolypeptide comprising Substructure IV, and water, wherein Substructure III is depicted as follows:

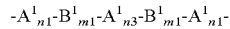   Substructure III;

Substructure IV is depicted as follows:

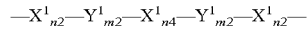   Substructure IV;

each instance of $A^1$ is an amino acid residue independently selected from a non-ionic, hydrophilic amino acid, sarcosine, glycine, and alanine;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1, n2, n3, and n4 is independently about 25 to about 600;
each m1 and m2 is independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked.

The present disclosure also provides methods of making and using the compositions disclosed herein.

DETAILED DESCRIPTION OF THE INVENTION

Figure 1:
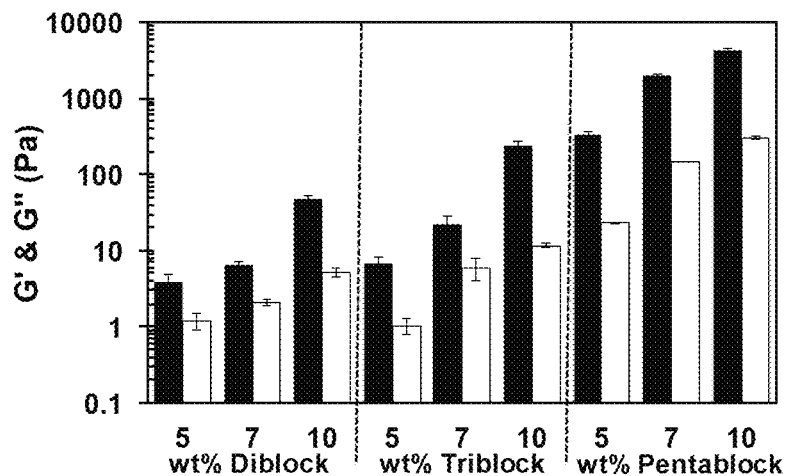
FIG. 1 depicts the mechanical properties of PIC block copolypeptide hydrogels. Storage modulus (G', Pa, black) and loss modulus (G", Pa, white) of diblock, triblock, and pentablock hydrogels were measured at varying sample concentrations in 1×PBS buffer at 25° C. All G' and G" values were measured at an angular frequency of 5 rad/s and a strain amplitude of 0.01.

Diblock copolypeptide PIC hydrogels (DCH$_{PIC}$) that utilize formation of β-sheet structured solid complexes are cell-compatible, self-healing, and resistant to dilution. In an effort to improve the efficiency of hydrogel formation and to enhance mechanical properties, disclosed herein are studies on the aqueous assembly of triblock and pentablock copolypeptides designed to form PIC hydrogels. These copolymers possess block architectures that have not previously been explored for PIC assembly, and were found to significantly enhance network formation and stiffness compared to diblock architectures at equivalent concentrations.

Most block copolymer PIC hydrogels have been prepared using one or two triblock copolymer components containing ionic end-blocks flanking a non-ionic, hydrophilic center block. These hydrogels rely on the formation of phase-separated, PIC liquid coacervate spherical domains that act as physical crosslinks in the networks, where the charged segments are placed as end-blocks to facilitate bridging of spherical domains by the non-ionic segments leading to network formation. Alternatively, hydrogels have also been prepared via the assembly of amphiphilic, hydrophobically assembled triblock copolymers in water, and these systems have recently incorporated more complex multiblock architectures to enhance and tune mechanical properties. It has been found that the use of multiblock and star copolymer architectures can enhance hydrogel properties in hydrophobically assembled copolypeptide systems. However, these amphiphilic materials can be difficult to formulate, especially at higher concentrations, and the reported systems are not cell compatible. Here, it was sought to develop PIC multiblock copolypeptide hydrogels that could overcome these issues and allow the preparation of hydrogels with a broad range of tunable properties. Since the assembly of DCH$_{PIC}$ in water promotes formation of solid PIC β-sheet fibrillar assemblies as opposed to the liquid coacervate spherical domains seen in other PIC hydrogels, the design of PIC multiblock copolypeptide architectures is modeled on related fibril forming amphiphilic block copolypeptide hydrogels as opposed to the more conventional triblock architectures used to form PIC hydrogels.

In one aspect, the present disclosure provides a composition comprising a first copolypeptide comprising Substructure I, and a second copolypeptide comprising Substructure II, and water, wherein Substructure I is depicted as follows:

    Substructure I;

-$A^1_{n1}$-$B^1_{m1}$-$A^1_{n1}$-

Substructure II is depicted as follows:

    Substructure II;

—$X^1_{n2}$—$Y^1_{m2}$—$X^1_{n2}$— each instance of $A^1$ is an amino acid residue independently selected from a non-ionic hydrophilic amino acid, sarcosine, glycine, and alanine;

in at least 20% of the instances of $B^1$, $B^1$ is an amino acid residue independently selected from an anionic hydrophilic amino acid or a salt thereof;

each instance of $X^1$ is an amino acid residue independently selected from a non-ionic hydrophilic amino acid, sarcosine, glycine, and alanine;

in at least 20% of the instances of $Y^1$, $Y^1$ is an amino acid residue independently selected from a cationic hydrophilic amino acid or a salt thereof;

each n1 and n2 is independently about 25 to about 600;

m1 and m2 are independently about 15 to about 600;

at least 75 mol % of the $B^1$ amino acid residues are (D)-amino acid residues or at least 75 mol % of the $B^1$ amino acid residues are (L)-amino acid residues;

at least 75 mol % of the $Y^1$ amino acid residues are (D)-amino acid residues or at least 75 mol % of the $Y^1$ amino acid residues are (L)-amino acid residues; and the first copolypeptide and the second copolypeptide are not covalently linked. In another aspect, the present disclosure provides composition comprising a first copolypeptide comprising Substructure III, and a second copolypeptide comprising Substructure IV, and water, wherein Substructure III is depicted as follows:

    Substructure III;

-$A^1_{n1}$-$B^1_{m1}$-$A^1_{n3}$-$B^1_{m1}$-$A^1_{n1}$-

Substructure IV is depicted as follows:

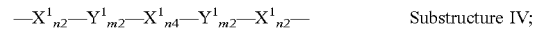    Substructure IV;

—$X^1_{n2}$—$Y^1_{m2}$—$X^1_{n4}$—$Y^1_{m2}$—$X^1_{n2}$— each instance of $A^1$ is an amino acid residue independently selected from a non-ionic, hydrophilic amino acid, sarcosine, glycine, and alanine;

in at least 20% of the instances of $B^1$, $B^1$ is an amino acid residue independently selected from an anionic hydrophilic amino acid or a salt thereof;

each instance of $X^1$ is an amino acid residue independently selected from a non-ionic hydrophilic amino acid, sarcosine, glycine, and alanine;

in at least 20% of the instances of $Y^1$, $Y^1$ is an amino acid residue independently selected from a cationic hydrophilic amino acid or a salt thereof;

each n1, n2, n3, and n4 is independently about 25 to about 600;

each m1 and m2 is independently about 15 to about 600;

at least 75 mol % of the $B^1$ amino acid residues are (D)-amino acid residues or at least 75 mol % of the $B^1$ amino acid residues are (L)-amino acid residues;

at least 75 mol % of the $Y^1$ amino acid residues are (D)-amino acid residues or at least 75 mol % of the $Y^1$ amino acid residues are (L)-amino acid residues; and the first copolypeptide and the second copolypeptide are not covalently linked.

In certain embodiments, each instance of $A^1$ is an amino acid residue independently selected from a non-ionic hydrophilic amino acid. In certain embodiments, each instance of $A^1$ is an amino acid residue independently selected from sarcosine, glycine, alanine, methionine sulfoxide, S-alkyl-cysteine sulfoxide, S-alkyl cysteine sulfone, S-alkyl-homocysteine, S-alkyl-homocysteine sulfoxide, glycosylated cysteine, serine, homoserine, and homomethionine sulfoxide. In certain embodiments, at least 90 mol % of the $A^1$ amino acid residues are (D)-amino acid residues. In other embodiments, at least 90 mol % of the $A^1$ amino acid residues are (L)-amino acid residues. In certain preferred embodiments, at least 85 mol % of the $A^1$ amino acid residues are methionine sulfoxide. In certain even further preferred embodiments, at least 85 mol % of the $A^1$ amino acid residues are methionine sulfoxide, and the remaining $A^1$ amino acid residues are alanine. In certain most preferred embodiments, about 88 mol % of the $A^1$ amino acid residues are methionine sulfoxide, and about 12 mol % of the $A^1$ amino acid residues are alanine.

In certain embodiments, each instance of $B^1$ is an amino acid residue independently selected from an anionic, hydrophilic amino acid. In certain embodiments, at least 90% of the $B^1$ amino acid residues are (D)-amino acid residues. In other embodiments, at least 90% of the $B^1$ amino acid residues are (L)-amino acid residues. In certain preferred embodiments, each instance of $B^1$ is glutamic acid or aspartic acid. In certain embodiments, each instance of $B^1$ is (L)-glutamic acid. In other embodiments, each instance of $B^1$ is (D)-glutamic acid.

In certain embodiments, each instance of $X^1$ is an amino acid residue independently selected from a non-ionic, hydrophilic amino acid. In certain embodiments, each instance of $X^1$ is an amino acid residue independently selected from sarcosine, glycine, alanine, methionine sulfoxide, S-alkyl-cysteine sulfoxide, S-alkyl cysteine sulfone, S-alkyl-homocysteine, S-alkyl-homocysteine sulfoxide, glycosylated cysteine, serine, homoserine, and homomethionine sulfoxide. In certain embodiments, at least 90 mol % of the $X^1$ amino acid residues are (D)-amino acid residues. In other embodiments, at least 90 mol % of the $X^1$ amino acid residues are (L)-amino acid residues. In certain preferred embodiments, at least 85 mol % of the $X^1$ amino acid residues are methionine sulfoxide. In certain even further preferred embodiments, at least 85 mol % of the $A^1$ amino acid residues are methionine sulfoxide, and the remaining $X^1$ amino acid residues are alanine. In certain most preferred embodiments, about 88 mol % of the $X^1$ amino acid residues are methionine sulfoxide, and about 12 mol % of the $A^1$ amino acid residues are alanine.

In certain embodiments, each instance of $Y^1$ is an amino acid residue independently selected from a cationic, hydrophilic amino acid. In certain embodiments, at least 90% of the $Y^1$ amino acid residues are (D)-amino acid residues. In other embodiments, at least 90% of the $Y^1$ amino acid residues are (L)-amino acid residues. In certain preferred embodiments, each instance of $Y^1$ is lysine, ornithine, or arginine. In certain even further preferred embodiments, each instance of $Y^1$ is (L)-lysine. In other even further preferred embodiments, each instance of $Y^1$ is (L)-lysine.

In certain embodiments, each n1 is independently about 20, about 30, about 40, about 50, about 60, about 70, about 80, about 90, or about 100. In certain preferred embodiments, n1 is about 50.

In certain embodiments, each m1 is independently about 10, about 20, about 30, about 40, about 50, or about 60. In certain preferred embodiments, m1 is about 30.

In certain embodiments, each n2 is independently about 20, about 30, about 40, about 50, about 60, about 70, about 80, about 90, or about 100. In certain preferred embodiments, n2 is about 50.

In certain embodiments, each m2 is independently about 10, about 20, about 30, about 40, about 50, or about 60. In certain preferred embodiments, m2 is about 30.

In certain embodiments, n3 is about 50, about 60, about 70, about 80, about 90, about 100, about 110, about 120, about 130, about 140, or about 150. In certain preferred embodiments, n3 is about 100.

In certain embodiments, n4 is about 50, about 60, about 70, about 80, about 90, about 100, about 110, about 120, about 130, about 140, or about 150. In certain embodiments, n4 is about 100.

In certain embodiments, the polydispersity of the first copolypeptide is less than 1.5. In certain embodiments, the polydispersity of the first copolypeptide is greater than 1.0.

In certain embodiments, the polydispersity of the second copolypeptide is less than 1.5. In certain embodiments, the polydispersity of the second copolypeptide is greater than 1.0.

In certain embodiments, the number of amino acid residues in the first copolypeptide is from about 90% to about 110% of the number of amino acid residues in the second copolypeptide.

In certain embodiments, the composition comprises $(M^OA)_{50}E_{30}(M^OA)_{50}$, $(M^OA)_{50}K_{30}(M^OA)_{50}$, $(M^OA)_{50}E_{30}(M^OA)_{100}E_{30}(M^OA)_{50}$, $(M^OA)_{50}K_{30}(M^OA)_{100}K_{30}(M^OA)_{50}$, $(M^OA)_{46}E_{27}(M^OA)_{52}$, $(M^OA)_{46}K_{29}(M^OA)_{49}$, $(M^OA)_{46}E_{28}(M^OA)_{89}E_{31}(M^OA)_{48}$, or $(M^OA)_{46}K_{29}(M^OA)_{95}K_{31}(M^OA)_{46}$.

In certain embodiments, the total concentration of the first copolypeptide and the second copolypeptide is about 1% to about 15 wt. %. In certain embodiments, the total concentration of the first copolypeptide and the second copolypeptide in the composition is about 5.0 wt. %. In other embodiments, the total concentration of the first copolypeptide and the second copolypeptide in the composition is about 7.0 wt. %. In yet other embodiments, the total concentration of the first copolypeptide and the second copolypeptide in the composition is about 10.0 wt. %.

In certain embodiments, the molar ratio of $A^1$ to $B^1$ is about 3:1 or about 4:1.

In certain embodiments, the molar ratio of $X^1$ to $Y^1$ is about 3:1 or about 4:1.

In certain embodiments, the composition further comprises a salt. In certain embodiments, the concentration of the salt in the composition is less than about 500 mM. In certain embodiments, the concentration of the salt in the composition is from about 100 mM to about 300 mM. In certain embodiments, the salt is NaCl.

In certain embodiments, the composition further comprises a buffer.

In certain embodiments, the composition further comprises a plurality of cells.

In certain embodiments, the composition has an increased loss modulus (G") as compared to a composition comprising a diblock polymer comprising the same or substantially similar amino acid residues; wherein both compositions are tested under substantially identical conditions (e.g., the temperature, % wt. of polymer in each composition, and ratio of amino acid components are substantially similar).

In certain embodiments, the composition has an increased storage modulus (G") as compared to a composition comprising a diblock polymer comprising the same or substantially similar amino acid residues; wherein both compositions are tested under substantially identical conditions (e.g., the temperature, % wt. of polymer in each composition, and ratio of amino acid components are substantially similar).

In certain embodiments, the composition has an increased elasticity as compared to a composition comprising a diblock polymer comprising the same or substantially similar amino acid residues; wherein both compositions are tested under substantially identical conditions (e.g., the temperature, % wt. of polymer in each composition, and ratio of amino acid components are substantially similar).

In another aspect, the present disclosure provides a method of making a composition of disclosure comprising:
dissolving the first copolypeptide in an aqueous medium; and
mixing the aqueous medium with a solution of the second copolypeptide, thereby forming the composition.

In yet another aspect, the present disclosure provides a method of making a composition of disclosure comprising:
dissolving the second copolypeptide in an aqueous medium; and
mixing the aqueous medium with a solution of the first copolypeptide, thereby forming the composition.

In certain embodiments, the aqueous medium further comprises an alcohol selected from methanol, ethanol, and isopropanol. In certain preferred embodiments, the alcohol is methanol. In certain embodiments, the aqueous medium comprises about 30% to about 70% methanol by volume. In certain embodiments, the aqueous medium comprises about 50% methanol by volume.

In certain embodiments, the mixing comprises rapid mixing, such as vortexing.

In yet another aspect, the present disclosure provides a method of delivering a drug to a biological target using a composition of the disclosure, the method comprising:
dissolving the drug in a first aqueous medium;
dissolving the first copolypeptide in the first aqueous medium, to form a second aqueous medium;
mixing the second aqueous medium with a solution of the second copolypeptide, thereby forming the composition encapsulating the drug; and
contacting the biological target with the composition with the drug.

In yet another aspect, the present disclosure provides a method of delivering a drug to a biological target using a composition of the disclosure, the method comprising:
dissolving the drug in a first aqueous medium;
dissolving the second copolypeptide in the first aqueous medium, to form a second aqueous medium;
mixing the second aqueous medium with a solution of the first copolypeptide, thereby forming the composition encapsulating the drug; and
contacting the biological target with the composition with the drug.

In certain embodiments, the biological target is a cell, organ, tissue, or protein.

In certain embodiments, the drug is hydrophobic. In certain embodiments, the drug is a chemotherapeutic agent. In certain embodiments, the drug is anthracycline. In certain embodiments, the drug is doxorubicin. In other embodiments, the drug is a hydrophilic drug. In certain embodiments, the hydrophilic drug is a protein or an antibody. In certain embodiments, the aqueous medium comprises an alcohol selected from methanol, ethanol, and isopropanol. In certain preferred embodiments, the alcohol is methanol.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The definition of each expression, e.g., alkyl, m, n, and the like, when it occurs more than once in any structure, is intended to be independent of its definition elsewhere in the same structure.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

The term "mixing" refers to any method of contacting one component of a mixture with another component of a mixture, including agitating, blending, combining, contacting, milling, shaking, sonicating, spraying, stirring, and vortexing.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

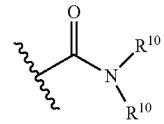

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

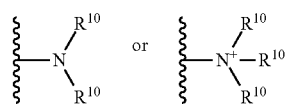

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

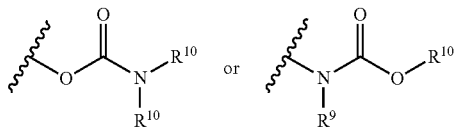

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings.

Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. Illustrative substituents include, for example, those described herein above. This invention is not intended to be limited in any manner by the permissible substituents of organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

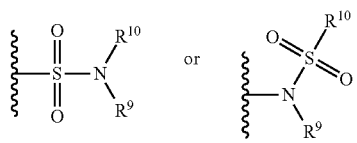

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

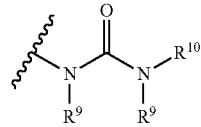

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

As used herein, the term "hydrophobic drug" refers to a drug (e.g., a small molecule) that is minimally or totally insoluble in an aqueous medium, such as water. Examples of hydrophobic drugs include, but are not limited to, anticancer agents such as paclitaxel, docetaxel, camptothecin, doxorubicin, daunomycin, cisplatin, 5-fluorouracil, mitomycin, methotrexate, and etoposide; antiinflammatory agents such as indomethacin, ibuprofen, ketoprofen, flubiprofen, dichlofenac, piroxicam, tenoxicam, naproxen, aspirin, and acetaminophen; antifungal agents such as itraconazole, ketoconazole and amphotericin; sex hormones such as testosterone, estrogen, progesterone, and estradiol; steroids such as dexamethasone, prednisolone, betamethasone, triamcinolone acetonide and hydrocortisone; antihypertensive agents such as ramipril, terazosin, minoxidil, and parazosin; antiemetics such as ondansetron and granisetron; antibiotics such as metronidazole, and fusidic acid; cyclosporines; prostaglandins; and biphenyl dimethyl dicarboxylic acid.

As used herein, the term "hydrophilic drug" refers to a drug (e.g., a small molecule) that possess a certain degree of solubility in an aqueous medium, such as water. Examples of hydrophilic drugs include, but are not limited to, albuterol, bendamustine, captopril, carboplatin, ciprofloxacin, gemcitabine, ibandronate, lamivudine, metformin, niacin, oxycodone, ranitidine and sumatriptan.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

Figure 4:
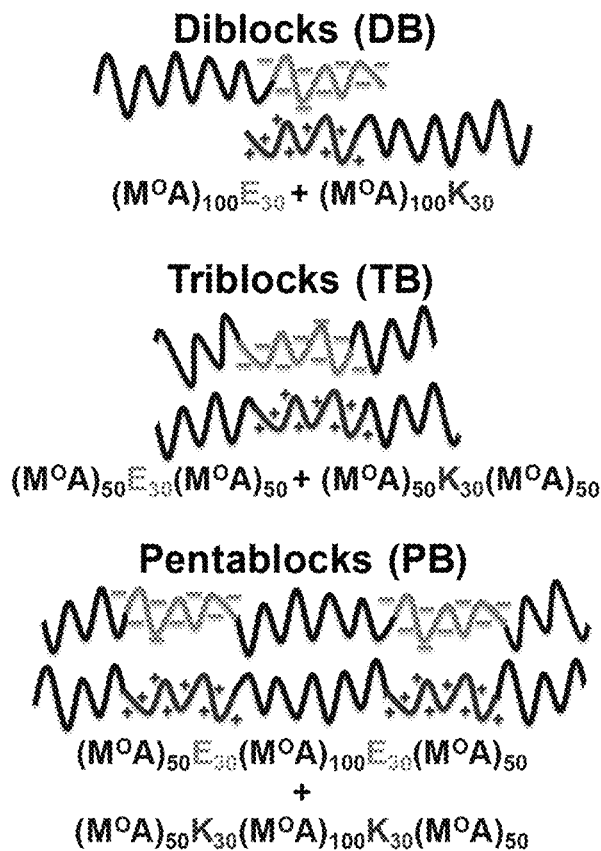
FIG. 4 is a schematic showing representations of diblock (DB), triblock (TB), and pentablock (PB) copolypeptides containing alternating non-ionic (MOA) and ionic (K or E) segments. Oppositely charged K and E domains in copolypeptides can assemble via PIC formation in aqueous media to give hydrogels.

The design of PIC multiblock copolypeptide hydrogels was based on triblock and pentablock amphiphilic block copopolypeptides that have previously been developed, where cationic and hydrophobic segments were replaced with non-ionic and ionic segments, respectively. The compositions of the non-ionic and ionic segments were based on those utilized previously in diblock $DCH_{PIC}$, namely poly(L-methionine sulfoxide-stat-L-alanine)$_{100}$-block-poly(L-lysine-HCl)$_{30}$, $(M^OA)_{100}K_{30}$, and poly(L-methionine sulfoxide-stat-L-alanine)$_{100}$-block-poly(L-glutamate-Na)$_{30}$, $(M^OA)_{100}E_{30}$ (Scheme 1). Notably, the triblock and pentablock copolypeptides were designed with non-associating (i.e. non-ionic) segments as end-blocks (Scheme 1 & FIG. 4), different from conventional PIC hydrogels that have associating ionic segments as end-blocks. This change is due to the different mechanism of assembly in $DCH_{PIC}$ compared to conventional PIC hydrogels, where the β-sheet structured solid PICs require substantial solubilizing segments to prevent further aggregation and precipitation.

The triblock and pentablock compositions were designed so that (i) their mole fractions of non-ionic and ionic residues would be identical to the diblock samples, and (ii) ionic segments would be roughly the same average length in all samples (Scheme 1). Matching of ionic and non-ionic copolypeptide content among all samples allows for meaningful and quantitative comparison of hydrogel properties since equivalent sample concentrations (wt %) will possess the same molar concentrations of amino acid components. Maintaining similar ionic segment lengths is also important since their variation has been shown to strongly affect hydrogel mechanical properties. The copolypeptides in Scheme 1 were prepared by the stepwise addition of appropriate NCA monomers to growing chains initiated using $Co(PMe_3)_4$, and gave samples with segment lengths and compositions that agreed well with the predicted values (see Table 1). Subsequent oxidation of methionine residues resulted in their conversion to methionine sulfoxides, and removal of protecting groups gave the final water soluble copolypeptides in high overall yields after purification (see Table 1).

Scheme 1. Chemical structures and compositions of diblock, triblock, and pentablock copolypeptides used in this study.
(A) cationic copolypeptides. (B) anionic copolypeptides.

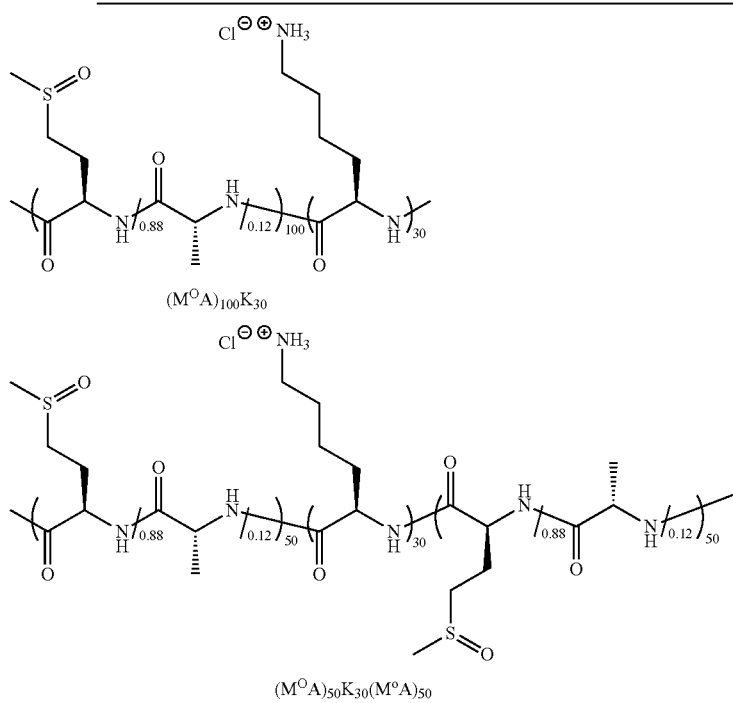

$(M^OA)_{100}K_{30}$ $(M^OA)_{50}K_{30}(M^OA)_{50}$

-continued
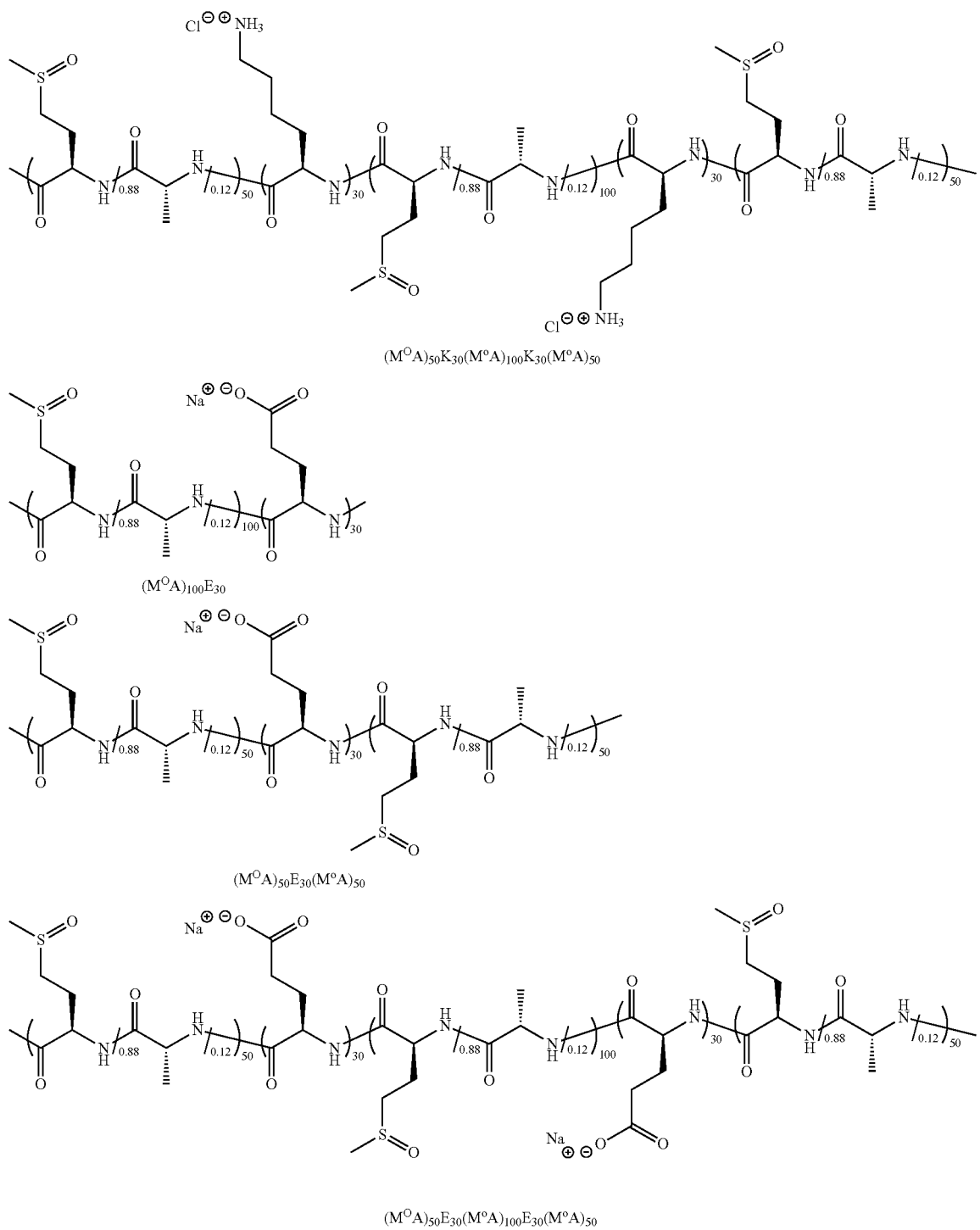
$(M^OA)_{50}K_{30}(M^OA)_{100}K_{30}(M^OA)_{50}$
$(M^OA)_{100}E_{30}$
$(M^OA)_{50}E_{30}(M^OA)_{50}$
$(M^OA)_{50}E_{30}(M^OA)_{100}E_{30}(M^OA)_{50}$
TABLE 1
Exemplary Block Polymers
| Sample | Mw/Mn[a] | Composition[b] | Yield (%)[c] |
|---|---|---|---|
| $(M^OA)_{100}E_{30}$ | 1.28 | $(M^OA)_{91}E_{26}$ | 95 |
| $(M^OA)_{100}K_{30}$ | 1.31 | $(M^OA)_{91}K_{28}$ | 93 |
| $(M^OA)_{50}K_{30}(M^OA)_{50}$ | 1.26 | $(M^OA)_{46}K_{29}(M^OA)_{49}$ | 92 |

TABLE 1-continued

Exemplary Block Polymers

| Sample | Mw/Mn[a] | Composition[b] | Yield (%)[c] |
|---|---|---|---|
| $(M^OA)_{50}E_{30}(M^OA)_{100}E_{30}(M^OA)_{50}$ | 1.36 | $(M^OA)_{46}E_{28}(M^OA)_{89}E_{31}(M^OA)_{48}$ | 91 |
| $(M^OA)_{50}K_{30}(M^OA)_{100}K_{30}(M^OA)_{50}$ | 1.32 | $(M^OA)_{46}K_{29}(M^OA)_{95}K_{31}(M^OA)_{46}$ | 93 |

[a]Dispersity of oxidized, protected block copolypeptides were determined by GPC/LS.
[b]Actual amino acid compositions of oxidized, deprotected block copolypeptides were determined by $^1$H NMR integrations. Degree of polymerization of initial $(MA)_x$ segments was determined by end-group analysis using $^1$H NMR.
[c]Total isolated yield of deprotected, purified block copolypeptides.

Materials and Instrumentation

Tetrahydrofuran (THF), hexanes, and methylene chloride were dried by purging with nitrogen and passage through activated alumina columns prior to use. $Co(PMe_3)_4$ and amino acid N-carboxyanhydride (NCA) monomers were prepared according to literature procedures. All other chemicals were purchased from commercial suppliers and used without further purification unless otherwise noted. Select silica gel 60 (particle size 0.032-0.063 mm) was used for flash column chromatography. Fourier transform infrared (FTIR) spectra were acquired on a Perkin Elmer RX1 FTIR spectrophotometer calibrated using polystyrene film, and attenuated total reflectance infrared (ATR-IR) data were collected using a Perkin Elmer Spectrum 100 FTIR spectrometer equipped with a universal ATR sample accessory. $^1$H NMR spectra were acquired on a Bruker ARX 400 spectrometer. Tandem gel permeation chromatography/light scattering (GPC/LS) was performed using an SSI Accuflow Series III pump equipped with Wyatt DAWN EOS light scattering and Optilab REX refractive index detectors. Separations were achieved using 100 Å and 1000 Å PSS-PFG 7 µm columns at 30° C. with 0.5% (w/w) KTFA in 1,1,1,3,3,3-hexafluoroisopropanol (HFIP) as eluent and sample concentrations of 10 mg/ml. Pyrogen free deionized (DI) water was obtained from a Millipore Milli-Q Biocel A10 purification unit.

General Procedure for Copolypeptide Synthesis

All polymerization reactions were performed in an $N_2$ filled glove box using anhydrous solvents. To a solution of L-methionine NCA (Met NCA) and L-alanine NCA (Ala NCA) in THF (50 mg/ml) was added a solution of $Co(PMe_3)_4$ in THF (20 mg/ml). The reactions were let to stir at ambient temperature (ca. 22° C.) for 60 min. Complete consumption of NCA was confirmed by FTIR spectroscopy, and then the desired amount of γ-benzyl-L-glutamate NCA (Bn-Glu NCA) or F-trifluoroacetyl-L-lysine NCA (TFA-Lys NCA) in THF (50 mg/ml) was added to the reaction mixtures, which were let to stir for an additional 60 min. FTIR was used to confirm complete consumption of all NCAs. Monomer additions were repeated as necessary. Once polymerizations were completed the block copolypeptide solutions were removed from the glove box, precipitated into 10 mM HCl (20 ml), and then washed with 10 mM aqueous HCl (2×20 ml) to remove residual cobalt ions. The white precipitates were then washed with DI water (3×20 ml) and freeze-dried to give products as white solids.[1] Subsequent oxidation of samples, followed by deprotection of Bn-Glu or TFA-Lys groups were performed as previously described.[2]

Poly(L-methionine sulfoxide$_{0.88}$-stat-L-alanine$_{0.12}$)$_{100}$-block-poly(L-lysine)$_{30}$, $(M^OA)_{100}K_{30}$ and poly(L-methionine sulfoxide$_{0.88}$-stat-L-alanine$_{0.12}$)$_{100}$-block-poly(L-glutamate)$_{30}$, $(M^OA)_{100}E_{30}$ These samples were prepared according to the methods described in Marciel, A. B.; Chung, E. J.; Brettmann, B. K.; Leon, L. Bulk and nanoscale polypeptide based polyelectrolyte complexes. Adv. Coll. Interface Sci. 2017, 239, 187-198, the contents of which are hereby fully incorporated by reference.

Poly(L-methionine sulfoxide$_{0.88}$-stat-L-alanine$_{0.12}$)$_{50}$-block-poly(L-lysine)$_{30}$-block-poly(L-methionine sulfoxide$_{0.88}$-stat-L-alanine$_{0.12}$)$_{50}$, $(M^OA)_{50}K_{30}(M^OA)_{50}$ and poly(L-methionine sulfoxide$_{0.88}$-stat-L-alanine$_{0.12}$)$_{50}$-block-poly(L-glutamate)$_{30}$-block-poly(L-methionine sulfoxide$_{0.88}$-stat-L-alanine$_{0.12}$)$_{50}$, $(M^OA)_{50}E_{30}(M^OA)_{50}$ In the glove box, a stock solution of Met NCA (110 mg, 0.62 mmol) mixed with Ala NCA (9.9 mg, 0.085 mmol) was prepared using THF (2.2 ml) and placed in a 20 ml scintillation vial. First block synthesis: The desired amount of Met/Ala NCA stock solution (1.2 ml) was added to a 20 ml scintillation vial containing a stir bar. To the vial, $(PMe_3)_4Co$ initiator solution (500 µl of a 20 mg/ml solution in THF) was added via syringe. The vial was sealed and allowed to stir in the glove box for 1 h. An aliquot (20 µl) was removed and analyzed by FTIR to confirm that all the NCA was consumed. In the glove box, α-methoxy-ω-isocyanoethyl-poly(ethylene glycol)$_{45}$ (mPEG$_{23}$-NCO) (20 mg) was dissolved in THF (1 ml) in a 20 ml scintillation vial. An aliquot (550 µl) of the polymerization solution containing active chain ends was removed and added to the solution of mPEG$_{23}$-NCO. The PEG end-capped sample (MA$_{50}$-mPEG$_{23}$) was sealed, allowed to stir for 24 h, and then used for chain length determination (vide infra). Second block synthesis: Separately, aliquots of the polymerization solution containing active chains (0.4 ml each) were added to vials containing either Bn-Glu NCA (21 mg, 0.078 mmol) or TFA-Lys NCA (21 mg, 0.078 mmol) dissolved in THF (410 µl or 420 µl, respectively). The vials were sealed and allowed to stir in the glove box for 1 h to give the diblock copolypeptides, (MA)$_{50}$(TFA-K)$_{30}$ and (MA)$_{50}$(Bn-E)$_{30}$. FTIR was used to confirm complete consumption of NCAs in both reactions. Aliquots (400 µl) of each polymerization solution were removed for $^1$H NMR analysis to determine the second block lengths. Third block synthesis: 470 µl of the Met/Ala NCA stock solution was added to each of the polymerization solutions to prepare the triblock copolypeptides, (MA)$_{50}$(TFA-K)$_{30}$(MA)$_{50}$ and (MA)$_{50}$(Bn-E)$_{30}$(MA)$_{50}$. The solutions were allowed to stir for 1 hr and were checked by FTIR to ensure completed NCA consumption. Outside the glove box, the triblock copolypeptide solutions were precipitated into 10 mM HCl (20 ml), and then washed with 10 mM aqueous HCl (2×20 ml) to remove residual cobalt ions. The white precipitates were then washed with DI water (3×20 ml) and freeze-dried (94% average yield). Subsequent oxidation of samples, followed by deprotection of Bn-Glu or TFA-Lys groups were performed as previously described.[2]

Poly(L-methionine sulfoxide$_{0.88}$-stat-L-alanine$_{0.12}$)$_{50}$-block-poly(L-lysine)$_{30}$-block-poly(L-methionine sulfoxide$_{0.88}$-stat-L-alanine$_{0.12}$)$_{100}$-block-poly(L-lysine)$_{30}$-block-poly(L-methionine sulfoxide$_{0.88}$-stat-L-alanine$_{0.12}$)$_{50}$, (M$^O$A)$_{50}$K$_{30}$(M$^O$A)$_{100}$K$_{30}$(M$^O$A)$_{50}$ and poly(L-methionine sulfoxide$_{0.88}$-stat-L-alanine$_{0.12}$)$_{50}$-block-poly(L-glutamate)$_{30}$-block-poly(L-methionine sulfoxide$_{0.88}$-stat-L-alanine$_{0.12}$)$_{100}$-block-poly(L-glutamate)$_{30}$-block-poly(L-methionine sulfoxide$_{0.88}$-stat-L-alanine$_{0.12}$)$_{50}$, (M$^O$A)$_{50}$E$_{30}$(M$^O$A)$_{100}$E$_{30}$(M$^O$A)$_{50}$ A stock solution of Met NCA (240 mg, 1.4 mmol) mixed with Ala NCA (22 mg, 0.19 mmol) was prepared using THF (4.8 ml) and placed in a 20 ml scintillation vial. 50 mg/ml stock solutions of Bn-Glu NCA (45 mg, 0.17 mmol) and TFA-Lys NCA (45 mg, 0.17 mmol) were also prepared using THF in 20 ml scintillation vials. First block synthesis: The desired amount of Met/Ala NCA stock solution (1.2 ml) was added to a 20 ml scintillation vial containing a stir bar. To the vial, (PMe$_3$)$_4$Co initiator solution (500 µl of a 20 mg/ml solution in THF) was added via syringe. The vial was sealed and allowed to stir in the glove box for 1 h. An aliquot (20 µl) was removed and analyzed by FTIR to confirm that all the NCA was consumed. In the glove box, α-methoxy-ω-isocyanoethyl-poly(ethylene glycol)$_{45}$ (mPEG$_{23}$-NCO) (20 mg) was dissolved in THF (1 ml) in a 20 ml scintillation vial. An aliquot (550 µl) of the polymerization solution containing active chain ends was removed and added to the solution of mPEG$_{23}$-NCO. The PEG end-capped sample (MA$_{50}$-mPEG$_{23}$) was sealed, allowed to stir for 24 h, and then used for chain length determination (vide infra). Second block synthesis: Separately, aliquots of the polymerization solution containing active chains (0.4 ml each) were added to vials containing either Bn-Glu NCA (410 µl of stock) or TFA-Lys NCA (420 µl of stock). The vials were sealed and allowed to stir in the glove box for 1 h to give the diblock copolypeptides, (MA)$_{50}$(TFA-K)$_{30}$ and (MA)$_{50}$(Bn-E)$_{30}$. FTIR was used to confirm complete consumption of NCAs in both reactions. Aliquots (400 µl) of each polymerization solution were removed for NMR analysis to determine the second block lengths. Third block synthesis: 470 µl of the Met/Ala NCA stock solution was added to each of the polymerization solutions to give the triblock copolypeptides, (MA)$_{50}$(TFA-K)$_{30}$(MA)$_{50}$ and (MA)$_{50}$(Bn-E)$_{30}$(MA)$_{50}$. The solutions were allowed to stir for 1 hr and were checked by FTIR to ensure completed NCA consumption. Aliquots (400 µl) of each polymerization solution were removed for $^1$H NMR analysis to determine the third block lengths. Fourth block synthesis: 180 µl of each Bn-Glu NCA and TFA-Lys NCA stock solution was added to the corresponding polymerization solution to give the tetrablock copolypeptides, (MA)$_{50}$(TFA-K)$_{30}$(MA)$_{50}$(TFA-K)$_{30}$ and (MA)$_{50}$(Bn-E)$_{30}$(MA)$_{50}$(Bn-E)$_{30}$. The solutions were allowed to stir for 1 hr and were checked by FTIR to ensure completed NCA consumption. Aliquots (400 µl) of each polymerization solution were removed for $^1$H NMR analysis to determine the fourth block lengths. Fifth block synthesis: 110 µl of the Met/Ala NCA stock solution was added to each of the polymerization solutions to give the final pentablock copolypeptides, (MA)$_{50}$(TFA-K)$_{30}$(MA)$_{50}$(TFA-K)$_{30}$(MA)$_{50}$ and (MA)$_{50}$(Bn-E)$_{30}$(MA)$_{50}$(Bn-E)$_{30}$(MA)$_{50}$. The solutions were allowed to stir for 24 hr and were checked by FTIR to ensure completed NCA consumption. Outside the glove box, the pentablock copolypeptide solutions were precipitated into 10 mM HCl (20 ml), and then washed with 10 mM aqueous HCl (2×20 ml) to remove residual cobalt ions. The white precipitates were then washed with DI water (3×20 ml) and freeze-dried (97% average yield). Subsequent oxidation of samples, followed by deprotection of Bn-Glu or TFA-Lys groups were performed as previously described in Sun, Y.; Wollenberg, A. L.; O'Shea, T. M.; Cui, Y.; Zhou, H.; Sofroniew, M. V.; Deming, T. J. J. Am. Chem. Soc. 2017, 139, 15114-15121, the contents of which are hereby fully incorporated by reference.

Example 2: Evaluation of Exemplary Compounds

Figure 5A:
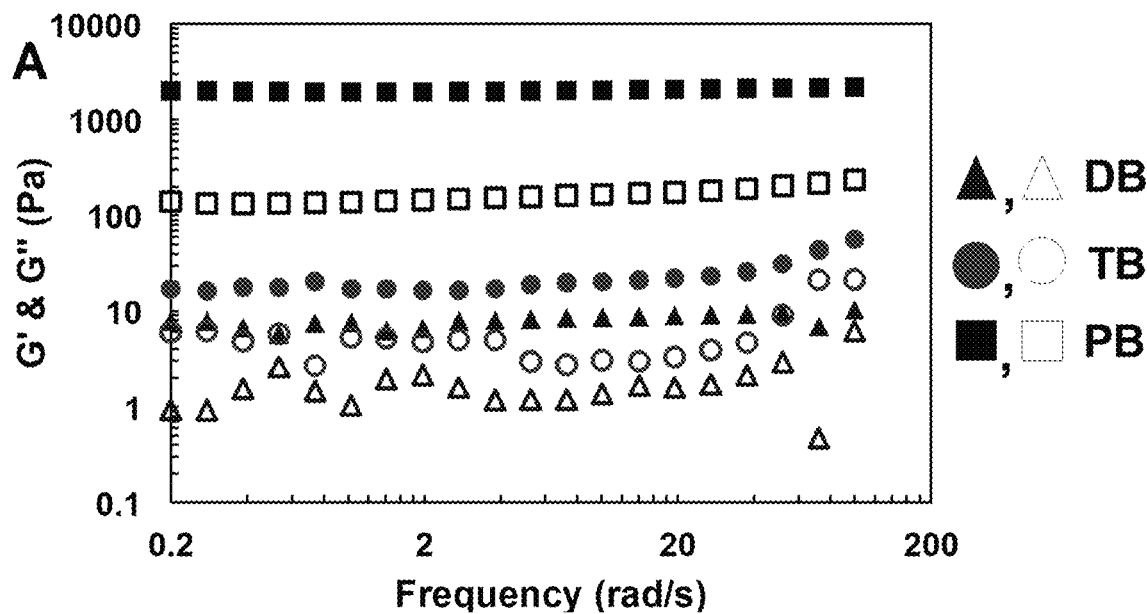
FIG. 5A depicts rheology data for PIC diblock (DB), triblock (TB) and pentablock (PB) hydrogels at 7 wt % in 1×PBS buffer at 20° C. G' (Pa, solid symbols) and G" (Pa, open symbols) of PIC block copolypeptide hydrogels as functions of angular frequency at constant strain amplitude of 0.01.
Figure 5B:
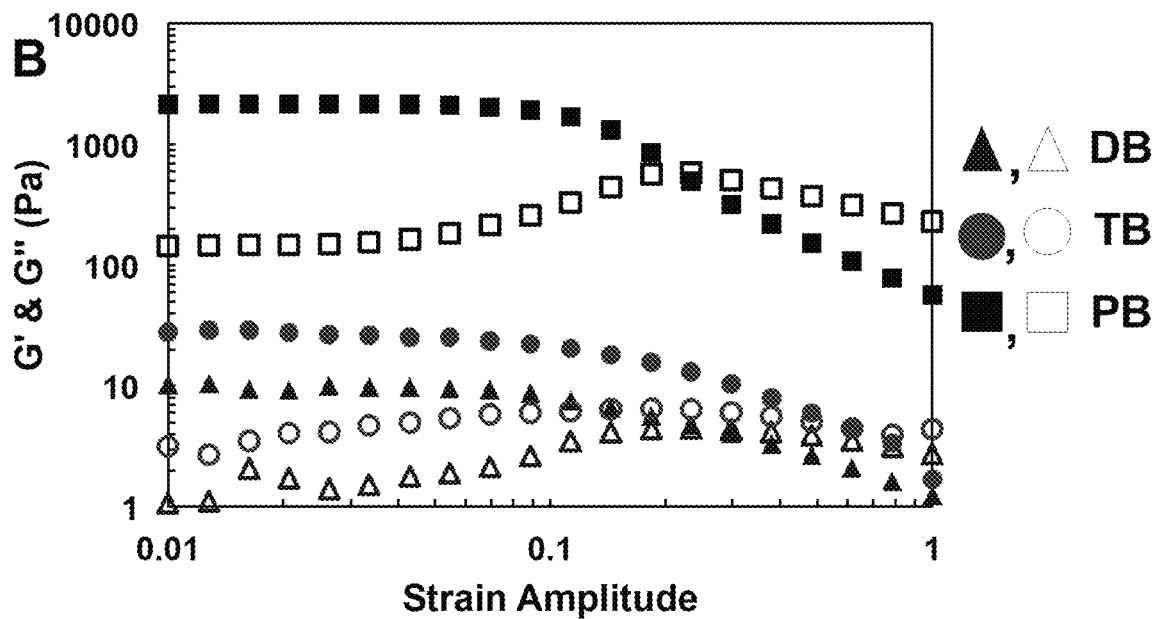
FIG. 5B depicts rheology data for PIC diblock (DB), triblock (TB) and pentablock (PB) hydrogels at 7 wt % in 1×PBS buffer at 20° C. Storage modulus, G' (Pa, solid symbols), and loss modulus, G" (Pa, open symbols), of PIC block copolypeptide hydrogels as functions of strain amplitude at a constant frequency of 5 rad/s.
Figures 6A, 6B, 6C:
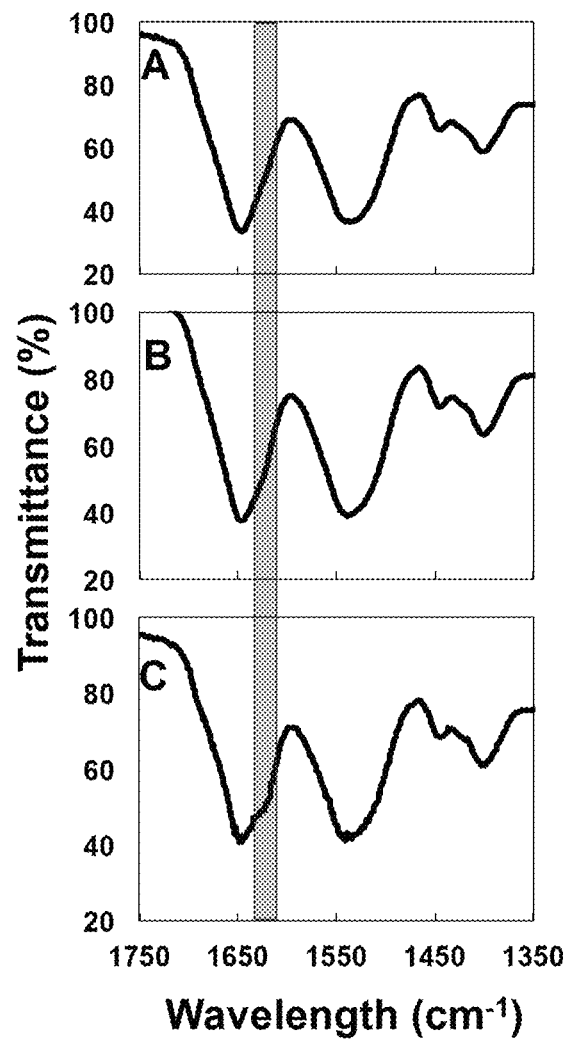
FIGS. 6A-6C is an ATR-IR spectra showing the amide region for lyophilized PIC (6A) diblock, (6B) triblock and (6C) pentablock copolypeptide hydrogel samples. Red box highlights area around 1630 cm$^{-1}$ Amide I band characteristic of β-sheet chain conformations. Amide I band at 1630 cm$^{-1}$ is more pronounced in pentablock sample (6C), suggesting increased β-sheet content compared to corresponding diblock and triblock samples. Note that the majority of polymer composition in all samples is the $(M^OA)_n$ segments, which are in disordered chain conformations and result in the large 1653 cm$^{-1}$ Amide I band.

PIC assemblies were prepared by mixing aqueous solutions (1×PBS) of matched diblock, triblock, or pentablock copolypeptides at different concentrations. Stoichiometric mixtures of oppositely charged copolypeptides resulted in the formation of transparent hydrogels within seconds to minutes depending on the concentration and block architecture, with pentablock samples forming hydrogels ca. 6 times faster than triblock and diblock samples. These samples were evaluated using oscillatory rheology to quantify their mechanical properties, and all were found to display elastic behavior (G'»G") over a range of frequency (FIG. 1, see FIGS. 5A & 5B). The hydrogels were also found to break down under high strain, as expected for physical hydrogels. While hydrogel stiffness (G') was found to increase with sample concentration for all samples, hydrogel stiffness of pentablock samples was always greater than triblock samples, and both were greater than diblock samples at equivalent concentrations (FIG. 2, see Table 2). Hence, multiblock architectures were found to allow the preparation of significantly stiffer hydrogels at equivalent amino acid contents and concentrations.

TABLE 2

Rheology data summary for PIC block copolypeptide hydrogels.

| Sample | wt % | G' (Pa) | G" (Pa) |
|---|---|---|---|
| Diblock | 5.0 | 3.93 | 1.19 |
| Diblock | 7.0 | 6.52 | 2.10 |
| Diblock | 10.0 | 47.1 | 5.12 |
| Triblock | 5.0 | 6.78 | 1.03 |
| Triblock | 7.0 | 22.5 | 5.84 |
| Triblock | 10.0 | 237 | 11.7 |
| Pentablock | 5.0 | 335 | 22.8 |
| Pentablock | 7.0 | 1990 | 147 |
| Pentablock | 10.0 | 4200 | 299 |

Data for 5 rad/s and strain amplitude = 0.01.

When comparing the diblock and triblock samples, both are composed of equal length chains. Here, the replacement of single long non-ionic segments in diblock samples with two shorter non-ionic segments in triblock samples is responsible for the observed modest increases in hydrogel stiffness. Although it has been found that longer non-associating (i.e. solubilizing) segment lengths in block copolypeptides enhance hydrogel formation, their effect on stiffness is relatively modest. Consequently, it is thought that the higher density of solubilizing segments per associating segment found in the triblock samples increases solubilizing chain steric repulsion at the block junctions upon PIC formation, resulting in formation of more extended, stiffer fibril assemblies.

Figure 7:
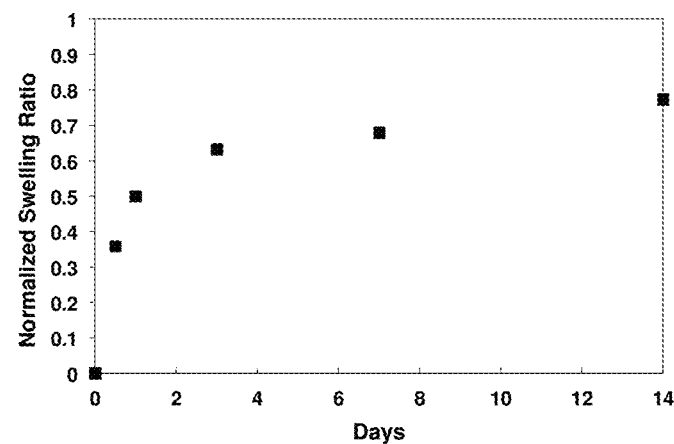
FIG. 7 shows normalized swelling ratio measurement. A sample of pentablock PIC hydrogel prepared at 10 wt % in 1×PBS was diluted with an equal volume of DMEM cell culture media. Hydrogel swelling was monitored by removal of all supernatant liquid above the hydrogel at different time points. Normalized swelling ratio was calculated as: (weight of sample after swelling−weight of initial hydrogel sample)/weight of initial hydrogel sample.
Figures 8A, 8B, 8C, 8D, 8E, 8F:
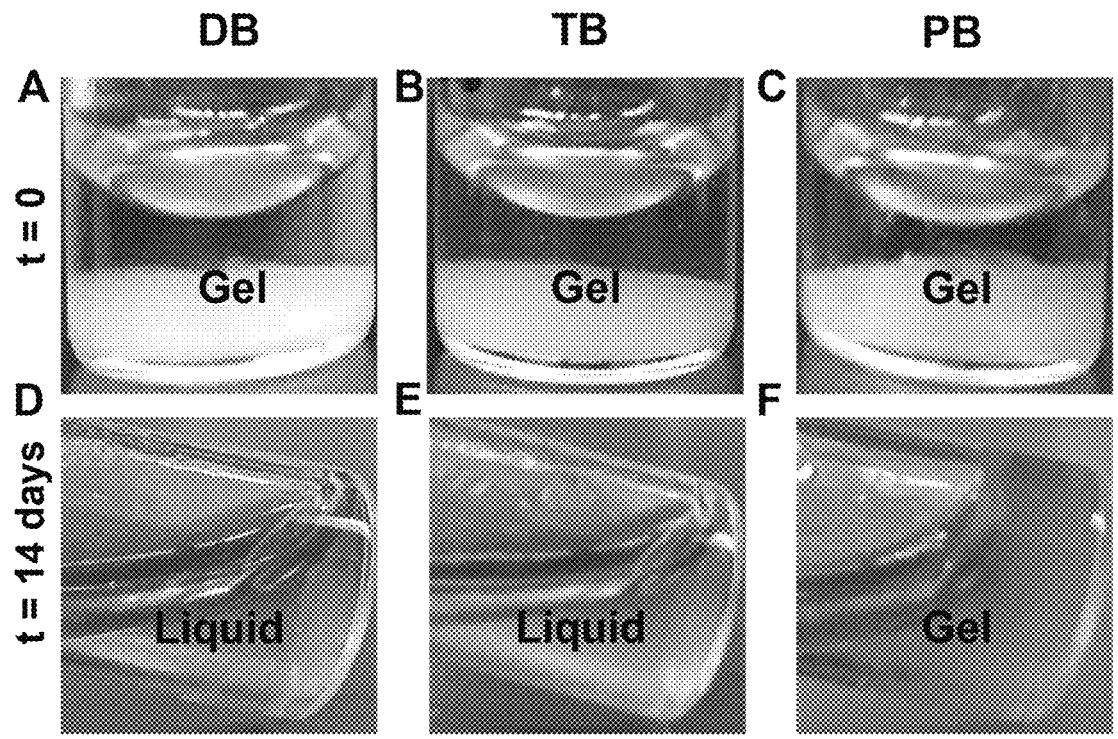
FIGS. 8A-8F shows the stability of multiblock PIC copolypeptide hydrogels against dilution. Diblock (DB), triblock (TB), and pentablock (PB) PIC hydrogels prepared at 10 wt % in 1×PBS were each diluted with an equal volume of DMEM cell culture media. (8A, 8B, 8C) A separate layer of cell media formed over all hydrogels at the beginning of the experiment (time=0). (8D, 8E, 8F) After 14 days, the pentablock hydrogel remained intact, while the diblock and triblock samples had dispersed into the media.
Figure 9:
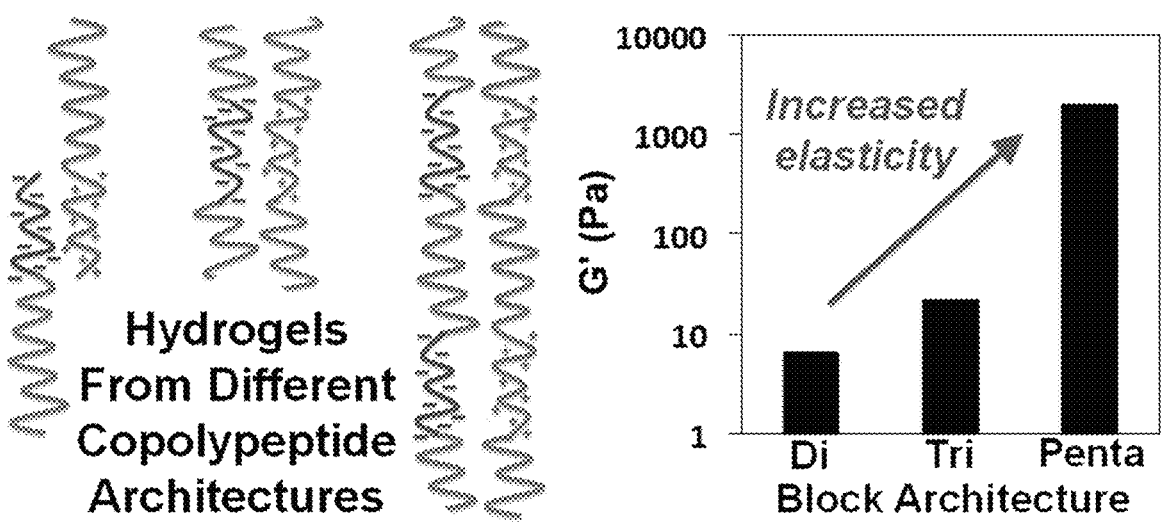
FIG. 9 depicts the improved properties of tri- and pentablock hydrogels as compared to diblock hydrogels.

The pentablock samples incorporate the features of the triblock samples, but also double the chain length. The presence of a central tether between associating domains also allows for bridging of fibrillar assemblies, and for and re-entry of chains into growing fibrils via chain folding during assembly. Based on results from assembly of hydrophobically assembled pentablock copolypeptide hydrogels, it was expected that the long central non-ionic tether segments present here will favor fibril re-entry over bridging, which was found previously to result in longer fibrils. The architectural features of the pentablock hydrogels resulted in their stiffness being up to ca. 100 times greater than equivalent concentration diblock samples. It was previously found that hydrogel formation in diblock samples was driven by the assembly of solid β-sheet structures in the PIC domains, which can be monitored by examination of polypeptide Amide I bands using FTIR spectroscopy. Analysis of lyophilized diblock, triblock, and pentablock samples revealed strong Amide I bands at 1653 $cm^{-1}$ due to the disordered chain conformations of the ($M^OA$) segments, and Amide I shoulders at 1630 $cm^{-1}$ that are characteristic of β-sheet chain conformations (See FIG. 7). The intensity of the band at 1630 $cm^{-1}$ was found to increase in samples from diblock to triblock to pentablock, consistent with improved β-sheet formation in the pentablock samples. Thus, it appears that pentablock samples allow for better chain ordering within the structured PIC domains, potentially due to kinetically favored chain re-entry during assembly, which results in substantial enhancement of hydrogel stiffness.

Figure 2A:
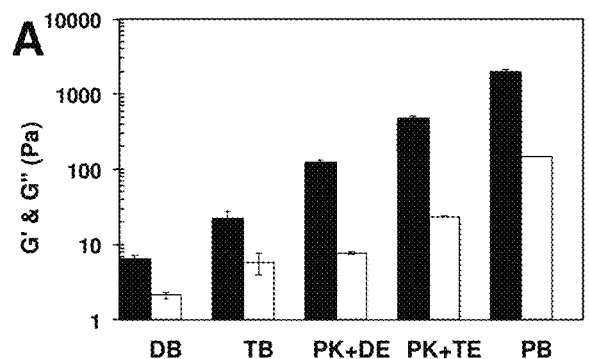
FIG. 2A depicts the mechanical properties of PIC block copolypeptide hydrogels prepared using matched and mismatched copolypeptides. (A) G' (Pa, black) and G" (Pa, white) of 7 wt % PIC hydrogels measured in 1×PBS buffer at 25° C. In matched samples, diblock (DB), triblock (TB), and pentablock (PB) hydrogels were prepared by mixing cationic and anionic copolypeptides of the same block architecture. In mismatched samples, cationic pentablock (PK) was mixed with either anionic diblock (DE) or anionic triblock (TE), where DE=$(M^OA)_{100}E_{30}$; TE=$(M^OA)_{50}E_{30}(M^OA)_{100}$; and PK=$(M^OA)_{50}K_{30}(M^OA)_{100}K_{30}(M^OA)_{50}$.
Figure 2B:
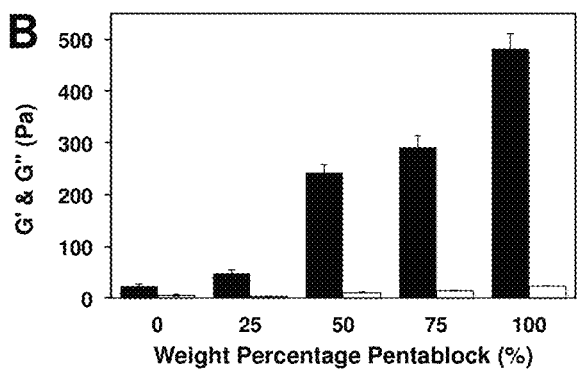
FIG. 2B mechanical properties of PIC block copolypeptide hydrogels prepared using matched and mismatched copolypeptides. G' (Pa, black) and G" (Pa, white) of 7 wt % PIC hydrogels (PK+TB), with varying weight % incorporation of cationic PK component into triblock mixtures, were measured in 1×PBS buffer at 25° C. All samples were prepared with stoichiometric E to K ratios. All G' and G" values were measured at an angular frequency of 5 rad/s and a strain amplitude of 0.01.

To evaluate interactions between different block architectures, charge balanced mixtures of cationic pentablock chains (i.e. PK) with anionic diblock (i.e. DE) or triblock (i.e. TE) chains were prepared. At 7.0 wt % in 1×PBS media, these 'mismatched' samples were found to form hydrogels with stiffness (G') intermediate between the matched diblock, triblock, and pentablock samples (FIG. 2A). In both cases, enhancement of stiffness was up to ca. 10 times greater compared to matched diblock and triblock samples. These results indicate that the different block copolypeptide architectures containing associating ionic segments of similar length can efficiently co-assemble into hydrogel networks. This behavior is similar to results obtained with amphiphilic copolypeptide hydrogels where samples with similar hydrophobic segment lengths could be mixed to tune mechanical properties. Such behavior is beneficial for the fine tuning of mechanical properties without having to prepare many different compositions, and potentially allows for significant enhancement of hydrogel stiffness using small amounts of multiblock copolypeptides. To test this concept, 7.0 wt % triblock hydrogels were prepared using increasing amounts (wt %) of cationic pentablock (i.e. PK) copolypeptides, where the amount of cationic triblock (i.e. TK) chains was simultaneously decreased in the formulations to maintain charge balance. The data in FIG. 2B shows that hydrogel stiffness can be enhanced as the fraction of cationic PK chains is increased, with a significant increase in stiffness when the fraction of PK is above 50 wt %.

Figure 3:
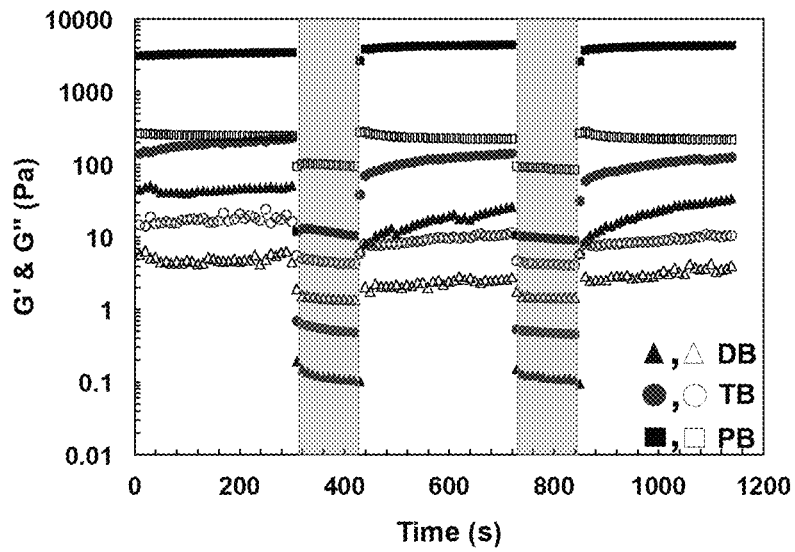
FIG. 3 depicts the mechanical recovery of diblock (DB), triblock (TB), and pentablock (PB) hydrogels. Samples prepared at 10 wt % in 1×PBS buffer at 25° C. (G'=solid symbols; G"=open symbols) after application of stepwise large-amplitude oscillatory breakdown (gray regions=strain amplitude of 10 at 10 rad/s for 120 s) followed by low-amplitude linear recovery (white regions=strain amplitude of 0.01 at 5 rad/s for 300 s).

It was previously observed that $DCH_{PIC}$ were able to rapidly self-heal after mechanical breakdown when subjected to high amplitude oscillatory strain. Rapid self-healing behavior is a desirable property in hydrogels as it allows deposition of hydrogel via injection through small bore needles, which has utility in biological applications as well as in additive manufacturing. Diblock, triblock, and pentablock hydrogel samples (at 10 wt %, chosen to obtain a reasonably stiff diblock hydrogel) were evaluated to determine if their self-healing properties were affected by block architecture. Each sample was subjected to high amplitude oscillatory strain, followed immediately by monitoring the recovery of elasticity over time by measuring G' at a much smaller strain amplitude (FIG. 3). During the initial 100 s of high strain amplitude, G' for all samples dropped substantially to below the level of G", indicating that they all became viscous liquids. Upon switching to low strain amplitude, all samples began recovering their elastic properties over time. Remarkably, the pentablock sample, which possessed the greatest stiffness, was the fastest (less than ca. 10 s) to fully recover its mechanical properties. For the diblock and triblock samples, recovery of elasticity continued to occur over a time scale of minutes. The rapid and complete self-healing of the pentablock hydrogels was unexpected due to their capacity to form network connections via bridging of PIC fibrils. A possible explanation for rapid self-healing may that the pentablock hydrogels contain few chains that form bridges between fibrils, and instead most chains form loops on individual fibrils via kinetically favored chain re-entry during fibril growth, similar to fibrillar assemblies in hydrophobically associated pentablock copolypeptides. The rapid self-healing properties of the pentablock hydrogels combined with the ability to prepare samples of high stiffness by varying concentration provide a promising combination of attributes for development of injectable or printable hydrogel scaffolds. Furthermore, for the compositions studied, the pentablock hydrogels were also found to be more resistant to dissolution in media compared to diblock and triblock samples (see FIGS. 7 & 8A-8F).

In summary, new triblock and pentablock copolypeptides capable of forming PIC hydrogels in aqueous media are disclosed herein. With a design based on previously reported $DCH_{PIC}$ and hydrophobically associated multiblock copolypeptides, the pentablock hydrogels were found to possess substantially enhanced stiffness compared to diblock and triblock samples at equivalent concentrations. In addition to adjusting concentration, hydrogel properties could also be tuned by mixing 'mismatched' block architectures in different ratios. All hydrogels were capable of rapid self-healing after deformation, with pentablock samples showing the fastest complete recovery. The use of multiblock architectures in PIC copolypeptide hydrogels was found to impart these physical assemblies with significantly enhanced mechanical properties, while retaining self-healing ability and stability against dilution in aqueous media. It is expected that the multiblock hydrogels will also possess good cell compatibility, similar to that shown for the diblock $DCH_{PIC}$.

Sample Procedure for $MA_x$ Chain Length Determination Using End-Group Analysis

Outside of the glove box, a PEG end-capped sample ($MA_x$-$mPEG_{23}$) from above was washed with 10 mM aqueous HCl (2×). After stirring for 1 h, $MA_x$-$mPEG_{23}$ was collected by centrifugation and washed with DI water (3×20 ml) to remove all non-conjugated $mPEG_{23}$-NCO. The remaining $MA_x$-$mPEG_{23}$ was then freeze-dried to remove residual $H_2O$. To determine $MA_x$ molecular weights ($M_n$), $^1H$ NMR spectra were obtained. Since it has been shown that end-capping is quantitative for $(PMe_3)_4Co$ initiated NCA polymerizations when excess isocyanate is used,[3] integrations of methionine (δ 2.70) and alanine (δ 1.52) resonances versus the polyethylene glycol resonance at δ 3.92 could be used to obtain both M to A ratios and $MA_x$ lengths.

Rheology Measurements on Block Copolypeptide Hydrogels

An Anton Paar Instruments MCR 302 rheometer with a 25 mm diameter and 10 cone plate geometry and solvent trap was used for all measurements. Frequency sweeps were measured at constant strain amplitude of 0.01. Strain sweeps were measured at a constant frequency of 5 rad/s. All measurements were repeated 3 times for each hydrogel sample and the results were averaged. To evaluate shear thinning and recovery behavior of DCH, the strain amplitude was stepped from 0.01 to 10, maintained at 10 for 2 min and then returned to 0.01 to evaluate the recovery of mechanical properties at a fixed frequency of 5 rad/s.

Hydrogel Swelling Measurements 10 wt % hydrogels of $(M^OA)_{100}E/K_{30}$, $(M^OA)_{50}K_{30}$ $(M^OA)_{50}$ and $(M^OA)_{50}K_{30}(M^OA)_{100}K_{30}(M^OA)_{50}$ were prepared in 2 ml scintillation vials and allowed to stand for 1 hr. DMEM cell culture media was then placed on top of each hydrogel sample and all were stored in a refrigerator (0° C.) for different periods of time. At each time point, the supernatant liquid was pipetted out of each sample without disturbing the gel at the bottom. The supernatant volumes were subtracted from the original media volume to determine swelling ratios. The hydrogel samples were also subjected to inversion tests to verify hydrogel integrity. Finally, the supernatant liquid was replaced on top of each hydrogel and incubation of samples allowed to continue.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A composition comprising:
i) a first copolypeptide comprising Substructure I, and a second copolypeptide comprising Substructure II, and water, wherein
Substructure I is depicted as follows:

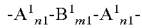   Substructure I;

Substructure II is depicted as follows:

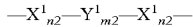   Substructure II;

each instance of $A^1$ is an amino acid residue independently selected from a non-ionic hydrophilic amino acid, sarcosine, glycine, and alanine;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1 and n2 is independently about 25 to about 600; m1 and m2 are independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked; or
ii) a first copolypeptide comprising Substructure III, and a second copolypeptide comprising Substructure IV, and water, wherein
Substructure III is depicted as follows:

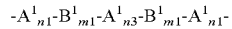   Substructure III;

Substructure IV is depicted as follows:

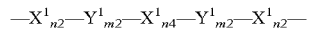   Substructure IV;

each instance of $A^1$ is an amino acid residue independently selected from a non-ionic, hydrophilic amino acid, sarcosine, glycine, and alanine;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1, n2, n3, and n4 is independently about 25 to about 600;
each m1 and m2 is independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked.

2. The composition of claim 1, wherein each instance of $A^1$ is an amino acid residue independently selected from a non-ionic hydrophilic amino acid.

3. The composition of claim 1, wherein each instance of $A^1$ is an amino acid residue independently selected from sarcosine, glycine, alanine, methionine sulfoxide, S-alkyl-cysteine sulfoxide, S-alkyl cysteine sulfone, S-alkyl-homocysteine, S-alkyl-homocysteine sulfoxide, glycosylated cysteine, serine, homoserine, and homomethionine sulfoxide.

4. The composition of claim 1, wherein at least 85 mol % of the $A^1$ amino acid residues are methionine sulfoxide.

5. The composition of claim 1, wherein each instance of $B^1$ is an amino acid residue independently selected from an anionic, hydrophilic amino acid.

6. The composition of claim 1, wherein each instance of $B^1$ is glutamic acid or aspartic acid.

7. The composition of claim 1, wherein each instance of $X^1$ is an amino acid residue independently selected from a non-ionic, hydrophilic amino acid.

8. The composition of claim 1, wherein each instance of $X^1$ is an amino acid residue independently selected from sarcosine, glycine, alanine, methionine sulfoxide, S-alkyl-cysteine sulfoxide, S-alkyl cysteine sulfone, S-alkyl-homocysteine, S-alkyl-homocysteine sulfoxide, glycosylated cysteine, serine, homoserine, and homomethionine sulfoxide.

9. The composition of claim 1, wherein at least 85 mol % of the $X^1$ amino acid residues are methionine sulfoxide.

10. The composition of claim 1, wherein each instance of $Y^1$ is an amino acid residue independently selected from a cationic, hydrophilic amino acid.

11. The composition of claim 1, wherein each instance of $Y^1$ is lysine, ornithine, or arginine.

12. The composition of claim 1, wherein each n1 is independently about 20, about 30, about 40, about 50, about 60, about 70, about 80, about 90, or about 100; each m1 is independently about 10, about 20, about 30, about 40, about 50, or about 60; each n2 is independently about 20, about 30, about 40, about 50, about 60, about 70, about 80, about 90, or about 100; each m2 is independently about 10, about 20, about 30, about 40, about 50, or about 60; n3 is about 50, about 60, about 70, about 80, about 90, about 100, about 110, about 120, about 130, about 140, or about 150; and n4 is about 50, about 60, about 70, about 80, about 90, about 100, about 110, about 120, about 130, about 140, or about 150.

13. The composition of claim 1, wherein the polydispersity of the second copolypeptide is less than 1.5.

14. The composition of claim 1, wherein the number of amino acid residues in the first copolypeptide is from about 90% to about 110% of the number of amino acid residues in the second copolypeptide.

15. The composition of claim 1, wherein the composition comprises $(M^OA)_{50}E_{30}(M^OA)_{50}$, $(M^OA)_{50}K_{30}(M^OA)_{50}$, $(M^OA)_{50}E_{30}(M^OA)_{100}E_{30}(M^OA)_{50}$, $(M^OA)_{50}K_{30}(M^OA)_{100}K_{30}(M^OA)_{50}$, $(M^OA)_{46}E_{27}(M^OA)_{52}$, $(M^OA)_{46}K_{29}(M^OA)_{49}$, $(M^OA)_{46}E_{28}(M^OA)_{89}E_{31}(M^OA)_{48}$, or $(M^OA)_{46}K_{29}(M^OA)_{95}K_{31}(M^OA)_{46}$.

16. The composition of claim 1, wherein the total concentration of the first copolypeptide and the second copolypeptide in the composition is about 1% to about 15 wt. %.

17. The composition of claim 1, wherein the molar ratio of $A^1$ to $B^1$ is about 3:1 or about 4:1.

18. The composition of claim 1, wherein the molar ratio of $X^1$ to $Y^1$ is about 3:1 or about 4:1.

19. A method of making a composition of claim 1 comprising either:
dissolving the first copolypeptide in an aqueous medium; and
mixing the aqueous medium with a solution of the second copolypeptide, thereby forming the composition; or
dissolving the second copolypeptide in an aqueous medium; and
mixing the aqueous medium with a solution of the first copolypeptide, thereby forming the composition.

20. A method of delivering a drug to a biological target using a composition of claim 1, the method comprising:
dissolving the drug in a first aqueous medium;
dissolving the first copolypeptide in the first aqueous medium, thereby forming a second aqueous medium;
mixing the second aqueous medium with a solution of the second copolypeptide, thereby forming a composition with the drug; and
contacting the biological target with the composition with the drug; or
dissolving the drug in a first aqueous medium;
dissolving the second copolypeptide in the first aqueous medium, thereby forming a second aqueous medium;
mixing the second aqueous medium with a solution of the first copolypeptide, thereby forming a composition with the drug; and
contacting the biological target with the composition with the drug.

21. The composition of claim 1, wherein the composition comprises a first copolypeptide comprising Substructure I, and a second copolypeptide comprising Substructure II, and water, wherein Substructure I is depicted as follows:

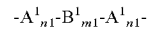

$$-A^1{}_{n1}\text{-}B^1{}_{m1}\text{-}A^1{}_{n1}\text{-} \qquad \text{Substructure I;}$$

Substructure II is depicted as follows:

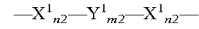

$$-X^1{}_{n2}-Y^1{}_{m2}-X^1{}_{n2}- \qquad \text{Substructure II;}$$

each instance of $A^1$ is an amino acid residue independently selected from a non-ionic hydrophilic amino acid, sarcosine, glycine, and alanine, provided that at least 85 mol % of the $A^1$ amino acid residues are methionine sulfoxide;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1 and n2 is independently about 25 to about 600;
m1 and m2 are independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked.

22. The composition of claim 1, wherein the composition comprises a first copolypeptide comprising Substructure III, and a second copolypeptide comprising Substructure IV, and water, wherein Substructure III is depicted as follows:

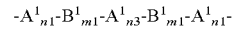

$$-A^1{}_{n1}\text{-}B^1{}_{m1}\text{-}A^1{}_{n3}\text{-}B^1{}_{m1}\text{-}A^1{}_{n1}\text{-} \qquad \text{Substructure III;}$$

Substructure IV is depicted as follows:

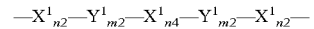

$$-X^1{}_{n2}-Y^1{}_{m2}-X^1{}_{n4}-Y^1{}_{m2}-X^1{}_{n2}- \qquad \text{Substructure IV;}$$

each instance of $A^1$ is an amino acid residue independently selected from a non-ionic, hydrophilic amino acid, sarcosine, glycine, and alanine, provided that at least 85 mol % of the $A^1$ amino acid residues are methionine sulfoxide;
in at least 20% of the instances of $B^1$, $B^1$ is an amino acid residue independently selected from an anionic hydrophilic amino acid or a salt thereof;
each instance of $X^1$ is an amino acid residue independently selected from a non-ionic hydrophilic amino acid, sarcosine, glycine, and alanine;
in at least 20% of the instances of $Y^1$, $Y^1$ is an amino acid residue independently selected from a cationic hydrophilic amino acid or a salt thereof;
each n1, n2, n3, and n4 is independently about 25 to about 600;
each m1 and m2 is independently about 15 to about 600;
at least 75 mol % of the $B^1$ amino acid residues are (D)-amino acid residues or at least 75 mol % of the $B^1$ amino acid residues are (L)-amino acid residues;
at least 75 mol % of the $Y^1$ amino acid residues are (D)-amino acid residues or at least 75 mol % of the $Y^1$ amino acid residues are (L)-amino acid residues; and
the first copolypeptide and the second copolypeptide are not covalently linked.

* * * * *